United States Patent
Akassoglou

(10) Patent No.: US 9,562,072 B2
(45) Date of Patent: Feb. 7, 2017

(54) COMPOSITIONS AND METHODS FOR REGULATING GLUCOSE METABOLISM

(71) Applicant: The J. David Gladstone Institutes, San Francsico, CA (US)

(72) Inventor: Katerina Akassoglou, San Francisco, CA (US)

(73) Assignee: The J. David Gladstone Institutes, San Francisco, CA (US)

(*) Notice: Subject to any disclaimer, the term of this patent is extended or adjusted under 35 U.S.C. 154(b) by 0 days.

(21) Appl. No.: 14/364,466

(22) PCT Filed: Dec. 20, 2012

(86) PCT No.: PCT/US2012/070887
§ 371 (c)(1),
(2) Date: Jun. 11, 2014

(87) PCT Pub. No.: WO2013/101645
PCT Pub. Date: Jul. 4, 2013

(65) Prior Publication Data
US 2014/0315799 A1    Oct. 23, 2014

Related U.S. Application Data

(60) Provisional application No. 61/580,523, filed on Dec. 27, 2011.

(51) Int. Cl.
| | | |
|---|---|---|
| *C07K 7/08* | (2006.01) | |
| *C07K 14/715* | (2006.01) | |
| *A61K 38/10* | (2006.01) | |
| *A61K 38/46* | (2006.01) | |
| *C12Q 1/54* | (2006.01) | |
| *G01N 33/60* | (2006.01) | |
| *G01N 33/66* | (2006.01) | |

(52) U.S. Cl.
CPC ............ *C07K 7/08* (2013.01); *A61K 38/10* (2013.01); *A61K 38/46* (2013.01); *C07K 14/7151* (2013.01); *C12Q 1/54* (2013.01); *C12Y 306/05002* (2013.01); *G01N 33/60* (2013.01); *G01N 33/66* (2013.01); *G01N 2500/00* (2013.01); *G01N 2800/042* (2013.01)

(58) Field of Classification Search
None
See application file for complete search history.

(56) References Cited

U.S. PATENT DOCUMENTS

| | | |
|---|---|---|
| 6,235,872 B1 | 5/2001 | Bredesen et al. |
| 2007/0166787 A1 | 7/2007 | Wallach et al. |
| 2009/0011501 A1 | 1/2009 | Reed et al. |
| 2011/0154522 A1 | 6/2011 | Korsmeyer et al. |

FOREIGN PATENT DOCUMENTS

| | | |
|---|---|---|
| JP | 02-069665 | 3/1990 |
| WO | WO 2008/022153 | 2/2008 |

OTHER PUBLICATIONS

Baeza-Raja et al. "Neurotrophin receptor regulates glucose homeostasis and insulin sensitivity", Proc Nat Acad Sci, 2012, vol. 109, No. 15, pp. 5838-5843.
Dugani, et al., "Glucose transporter 4: cycling, compartments and controversies" Embo Reports, 2005, vol. 6, No. 12, pp. 1137-1142.
Liepinsh et al. "NMR structure of the death domain of the p75 neurotrophin receptor" The EMBO Journal,1997,vol. 16, No. 16, pp. 4999-5005.
Lodhi et al. "Gapex-5, a Rab31 guanine nucleotide exchange factor that regulates Glut4 trafficking in adipocytes" Cell Metab, 2007, vol. 5, No. 1,pp. 59-72.
Passino, et al., "Regulation of Hepatic Stellate Cell Differentiation by the Neurotrophin Receptor p75", Science, 2007, vol. 315, 15 pages.
Peeraully et al. "NGF gene expression and secretion in white adipose tissue: Regulation in 3T3-L1 adipocytes by hormones and inflammatory cytokines" Am J Physiol Endocrinol Metab, 2004, vol. 287, pp. E331-E339.
Sachs et al. "p75 neurotrophin receptor regulates tissue fibrosis through inhibition of plasminogen activation via a PDE4/cAMP/PKA pathway" J Cell Biol, 2007, vol. 177, No. 6, pp. 1119-1132.
UniProt TNR16_HUMAN, Nov. 16, 2011 [online]. [Retrieved Apr. 26, 2013]. Retrieved from the internet: <URL: http://www.uniprot.org/uniprot/P08138.txt?version=134>. Especially p. 5 AA 386-400.
Yamashita, et al. "Neurotrophin Binding to the p75 Receptor Modulates Rho Activity and Axonal Outgrowth" Neuron, 1999, vol. 24, pp. 585-593.
Baeza-Raja et al.: "p75 neurotrophin receptor regulates glucose homeostasis and insulin sensitivity", Proc Nat Acad Sci, vol. 109, No. 15, Apr. 10, 2012, pp. 5838-5843, XP055075335, "I".
Blochl et al: "Inactivation and activation of Ras by the neurotrophin receptor p75", European Journal of Neuroscience, vol. 20, No. 9, Nov. 1, 2004, pp. 2321-2335, XP55170999, ISSN: 0953-816X, DOI: 10.1111 /j.1460-9568.2004.03692.x.
Tan et al: "Nerve Growth Factor Blocks the Glucose-induced Downregulation of Caveolin-1 Expression in Schwann Cells via p75 Neurotrophin Receptor Signaling", Journal of Biological Chemistry, vol. 278, No. 25, Jun. 13, 2003, pp. 23151-23162, XP55171007, ISSN: 0021-9258, DOI: 10.1074/jbc.M212986200.
"UPIOOOOE03CE4", Uni Prat, Mar. 23, 2007, XP002736199, Retrieved from the Internet: URL:http://www.uniprot.org/uniparc/UPIOOOOE03CE4 [retrieved on Feb. 19, 2015].

*Primary Examiner* — James H Alstrum Acevedo
*Assistant Examiner* — Tara Martinez
(74) *Attorney, Agent, or Firm* — Michael B. Rubin; Bozicevic, Field & Francis LLP

(57) ABSTRACT

The present disclosure provides compositions for regulating glucose metabolism. The compositions provide for reduced levels of p75$^{NTR}$ and/or reduced binding of p75$^{NTR}$ to a GTPase such as Rab31 or Rab5. The compositions are useful in methods of regulating glucose metabolism, which methods are also provided.

8 Claims, 15 Drawing Sheets

Homo sapiens p75^NTR
GenBank NP_002498

```
  1 mgagatgram dgprlllll1 lgvslggake acptglyths gecckacnlg egvaqpcgan
 61 qtvcepclds vtfsdvvsat epckpctecv glqsmsapcv eaddavcrca ygyyqdettg
121 rceacrvcea gsglvfscqd kqntvceecp dgtysdeanh vdpclpctvc edterqlrec
181 trwadaecee ipgrwitrst ppegsdstap stqepeappe qdliastvag vvttvmgssq
241 pvvtrgttdn lipvycsila avvvglvayi afkrwnsckq nkqgansrpv nqtpppegek
301 lhsdsgisvd sqslhdqqph tqtasgqalk gdgglysslp pakreevekl lngsagdtwr
361 hlagelgyqp ehidsfthea cpvrallasw atqdsatlda llaalrriqr adlveslcse
421 statspv
``` death domain – bold and underlined

FIG. 11

```
human  GGLYSSLPPAKREEVEKLLNGSAGDTWRHLAGELGYQPEHIDSFTHEACPVRALLASWAT 60
chimp  GGLYSSLPPAKREEVEKLLNGSAGDTWRHLAGELGYQPEHIDSFTHEACPVRALLASWAT 60
dog    GGLYSSLPPAKREEVEKLLNGSAGDTWRHLAGELGYQPEHIDSFTHEACPARALLASWAA 60
rat    GNLYSSLPLTKREEVEKLLN---GDTWRHLAGELGYQPEHIDSFTHEACPVRALLASWGA 57
mouse  GNLYSSLPLTKREEVEKLLN---GDTWRHLAGELGYQPEHIDSFTHEACPVRALLASWGA 57
       *:******* ********** ***************************.********..

human  QDSATLDALLAALRRIQRADIVESLCSESTATSPV 95
chimp  QDSATLDALLAALRRIQRADIVESLCSESTATSPV 95
dog    QDSATLDALLAALRRIQRADIVESLCSESTATSPV 95
rat    QDSATLDALLAALRRIQRADIVESLCSESTATSPV 92
mouse  QDSATLDALLAALRRIQRADIVESLCSESTATSPV 92
       **********************************
```

FIG. 12

Rab5 GTPase
Homo sapiens
GenBank AAB08927

```
  1 magrggarrp ngpaagnkic qfklvllges avgksslvlr fvkgqfheyq estigaaflt
 61 qtvclddttv kfeiwdtagq eryhslapmy yrgaqaaivv yditntdtfa raknwvkelq
121 rqaspnivia lagnkadlas kravefqeaq ayaddnsllf metsaktamn vneifmaiak
181 klpknepqna tgapgrnrgv dlqennpasr sqccsn
```

FIG. 13

Rab31 GTPase
Homo sapiens
GenBank NP_006859

```
  1 mmairelkvc llgdtgvgks sivcrfvqdh fdhnisptig asfmtktvpc gnelhkfliw
 61 dtaggerfhs lapmyyrgsa aavivyditk qdsfytlkkw vkelkehgpe nivmaiagnk
121 cdlsdirevp lkdakeyaes igaivvetsa knainieelf ggisrqippl dphengnngt
181 ikvekptmqa srcc
```

FIG. 14

GenBank NM_002507.3
Homo sapiens p75NTR

```
   1 atggggcag gtgccaccgg ccgcgccatg gacgggccgc gcctgctgct gttgctgctt
  61 ctggggtgt cccttggagg tgccaaggag tgcatgccca caggcctgta cacacacagc
 121 ggtgatgct gcaaagcctg caacctgggc gagggtgtgg cccagccttg tggagccaac
 181 cagaccgtgt gtgagccctg tctggacagc gtgacgttct cccgacgtgg t gagcgcgac
 241 gagccgtgca gccgtgcac cgagtgcgtg gggctccaga gcatgtcggc gcctgtgtg
 301 gaggccgacg acgccgtgtg ccgctgcgcc tacggctact accaggatga gacgactggg
 361 cgctgcgagg cgtgccgcgt gtgcgaggcg ggctcgggcc tcgtgttctc ctgccaggac
 421 aagcagaaca ccgtgtgcga ggagtgcccc gaggacacg tccgtttctc ctgccaggac
 481 gtggacccgt gcctgcctg caccgtgtgc gaggagagat tccgacga agcgccagct ccggcgagtgc
 541 acacgctggg ccgagccga gtgcgaggag atccctgcc gttggattac acggtccaca
 601 ccccagagg gctcggacac cacaccccc agcaccagg agcctgaggc acctcccag
 661 caagacctca tagccagcac ggtgcaggt gtggtgacca cagtgatggg cagctcccgct
 721 cccgtgtga cccgaggcac ccgagcac ctcatccctg tctattgctc catcctggct
 781 gctgtggttg tgggcctttg tgggcctttgt ggcctacata gccttcaaga ggtgaacag ctgcaagcag
 841 aacaagcaag gagcaacag ccggcaagtg aaccagacgc ccccaccaga gggagaaaaa
 901 ctccacagcg acagtggcat ctccgtgac agccagagcc tgcatgacca gcagcccac
 961 acgcagacag cctcgggcca ggccctcaag ggtgacggag gcctctacag cagcctgccc
1021 ccagccaagc gggaggaggt ggagaagctt ctcaacgct ctgcggga cacctggcgg
1081 cacctggcgg gcgagctggg cgcccctggg ctaccagcc gagcacatag actccttttac ccatgaggcc
1141 tgcccgttc gcgcctgct tgcaagctgg gccaaccagg acagcgccac actggacgcc
1201 ctcctgccg cccctgcgcg catccagccga gccgacctcg tggagagtct gtgcagtgag
1261 tccactgcca catccccggt gtga
```

FIG. 15

COMPOSITIONS AND METHODS FOR REGULATING GLUCOSE METABOLISM

CROSS-REFERENCE

This application claims the benefit of U.S. Provisional Patent Application No. 61/580,523, filed Dec. 27, 2011, which application is incorporated herein by reference in its entirety.

STATEMENT REGARDING FEDERALLY SPONSORED RESEARCH

This invention was made with government support under Grant No. NS51470 awarded by the National Institutes of Health. The government has certain rights in the invention.

BACKGROUND

Insulin resistance is a key feature of type 2 diabetes, and is characterized by decreased glucose disposal, increased hepatic glucose production, with a reduced ability of insulin to maintain normal glucose homeostasis. Whole-body glucose metabolism is regulated by a complex communication network between various tissues, including adipose tissue, liver, muscle, and brain. Glucose transporter-4 (GLUT4) is the principal insulin-stimulated glucose transporter expressed primarily in adipose tissue and skeletal muscle. Insulin stimulates glucose uptake by inducing GLUT4 translocation to the plasma membrane. GLUT4 trafficking from intracellular compartments to the plasma membrane is regulated by a number of small GTPases, including Rab5 and its family member Rab31.

$p75^{NTR}$ is a member of the Tumor Necrosis Factor (TNF) receptor superfamily that was originally identified as a receptor for neurotrophins $p75^{NTR}$ is expressed in the nervous system and in adult non-neuronal tissues, such as white adipose tissue (WAT), and muscle. $p75^{NTR}$ has surprisingly diverse cellular functions, including modulation of cell survival, apoptosis and differentiation, which underlie its in vivo biologic functions, including liver and muscle regeneration, extracellular matrix remodeling, sensory neuron development, hypoxia, and the angiogenic response.

Literature

Dugani and Klip (2005) *EMBO Rep* 6:1137-1142; Lodhi et al. (2007) *Cell Metab* 5:59-72; Peeraully et al. (2004) *Am J Physiol Endocrinol Metab* 287:E331-339; Sachs et al. (2007) *J Cell Biol* 177:1119-1132; Liebinsh et al. (1997) *EMBO J.* 16:4999; Yamashita and Tohyama (2003) *Nat Neurosci* 6:461-467

SUMMARY

The present disclosure provides compositions for regulating glucose metabolism. The compositions provide for reduced levels of $p75^{NTR}$ and/or reduced binding of $p75^{NTR}$ to a GTPase such as Rab31 or Rab5. The compositions are useful in methods of regulating glucose metabolism, which methods are also provided.

BRIEF DESCRIPTION OF THE DRAWINGS

FIG. 3D depicts western blot analysis for $p75^{NTR}$ in mouse embryonic fibroblast (MEF)-derived adipocytes.

FIG. 9H depicts Peptide 2: NSRPVNQPRPEGEK (SEQ ID NO:33); Peptide 4: GQALKGDGGLYSSLP (SEQ ID NO:34); and Peptide 7: LLASWATQDSATLDA (SEQ ID NO:1).

FIGS. 10A-D depict aspects of the interaction of $p75^{NTR}$ with Rab5 and Rab31 GTPases.

FIG. 11 provides an amino acid sequence of a $p75^{NTR}$ polypeptide (SEQ ID NO:45)

FIG. 12 provides an amino acid sequence alignment of the death domain of $p75^{NTR}$ of various species. Human (SEQ ID NO:46); Chimp (SEQ ID NO:47); Dog (SEQ ID NO:48); Rat (SEQ ID NO:49); Mouse (SEQ ID NO:50).

FIG. 13 provides an amino acid sequence of a Rab5 GTPase (SEQ ID NO:51).

FIG. 14 provides an amino acid sequence of a Rab31 GTPase (SEQ ID NO:52).

FIG. 15 provides a nucleotide sequence encoding a $p75^{NTR}$ polypeptide (SEQ ID NO:53).

DEFINITIONS

Figure 1:
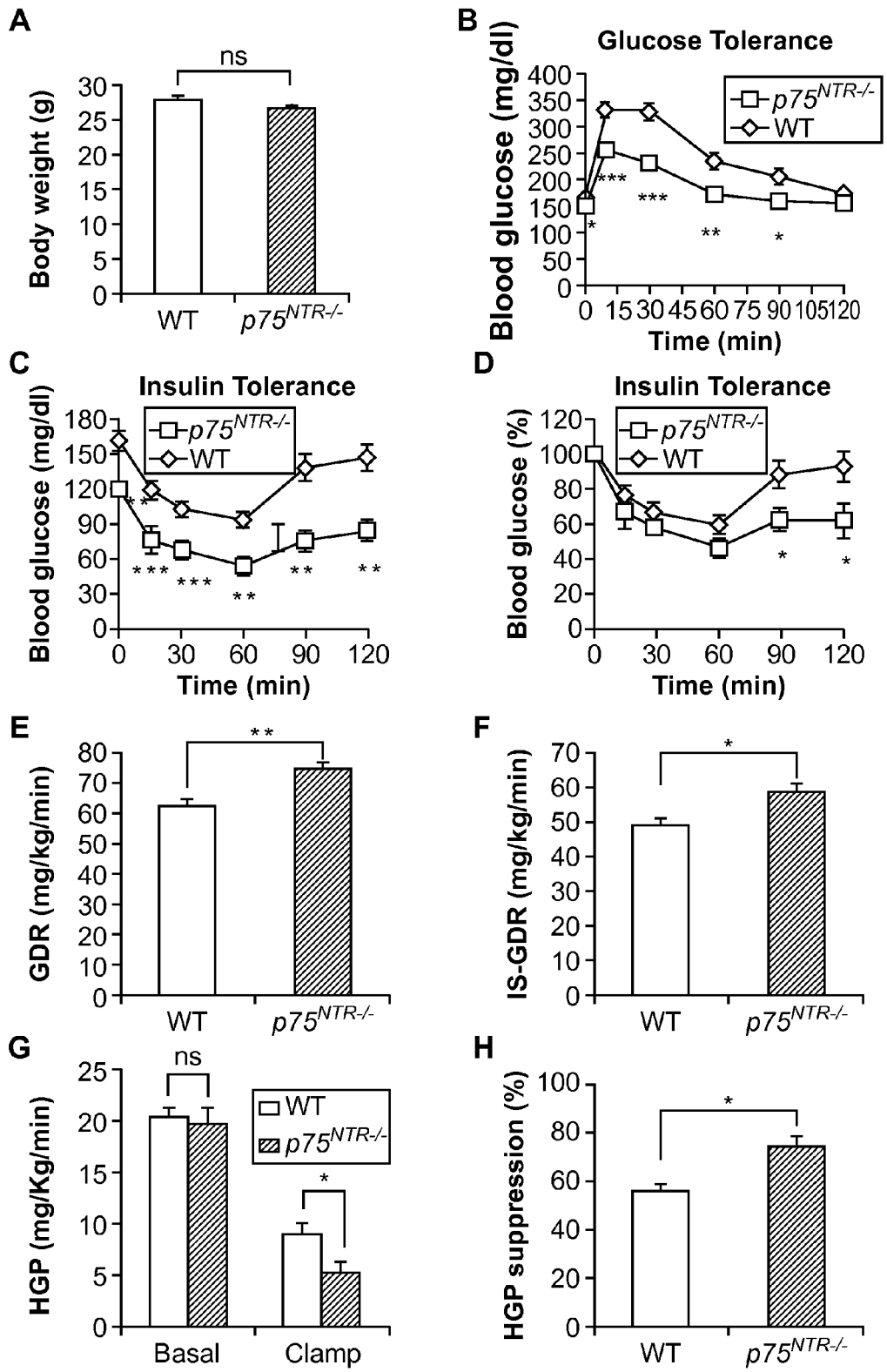
FIGS. 1A-H depict features of $p75^{NTR-/-}$ mice.

The phrase "glucose tolerance", as used herein, refers to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

The phrase "pre-diabetes", as used herein, refers a condition that may be determined using either the fasting plasma glucose test (FPG) or the oral glucose tolerance test (OGTT). Both require a person to fast overnight. In the FPG test, a person's blood glucose is measured first thing in the morning before eating. In the OGTT, a person's blood glucose is checked after fasting and again 2 hours after drinking a glucose-rich drink. In a healthy individual, a normal test result of FPG would indicate a glucose level of below about 100 mg/dl. A subject with pre-diabetes would have a FPG level between about 100 and about 125 mg/dl. If the blood glucose level rises to about 126 mg/dl or above, the subject is determined to have "diabetes". In the OGTT, the subject's blood glucose is measured after a fast and 2 hours after drinking a glucose-rich beverage. Normal blood glucose in a healthy individual is below about 140 mg/dl 2 hours after the drink. In a pre-diabetic subject, the 2-hour blood glucose is about 140 to about 199 mg/dl. If the 2-hour blood glucose rises to 200 mg/dl or above, the subject is determined to have "diabetes".

The term "Rab5 GTPase" refers to a polypeptide having GTPase activity, and sharing at least about 75%, at least about 85%, at least about 90%, at least about 95%, at least about 98%, at least about 99%, or 100%, amino acid sequence identity with a contiguous stretch of from about 150 amino acids to about 200 amino acids, or from about 200 amino acids to about 215 amino acids, of the amino acid sequence depicted in FIG. 13 (SEQ ID NO:51). See also GenBank Accession No. AAB08927; and GenBank Accession No. NP_080163. The crystal structure of human Rab5 has been reported; see, e.g., Zhu et al. (2003) *J. Biol. Chem.* 278:2452.

The term "Rab31 GTPase" refers to a polypeptide having GTPase activity, and sharing at least about 75%, at least about 85%, at least about 90%, at least about 95%, at least about 98%, at least about 99%, or 100%, amino acid sequence identity with a contiguous stretch of from about 125 amino acids to about 150 amino acids, from about 150 amino acids to about 175 amino acids, or from about 175 amino acids to about 195 amino acids, with the amino acid sequence depicted in FIG. 14 (SEQ ID NO:52). See also GenBank Accession No. CAG38587; and GenBank Accession No. NP_598446; and Bao et al. (2002) *Eur. J. Biochem.* 269:259.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a p75$^{NTR}$-derived peptide" includes a plurality of such peptides and reference to "the p75$^{NTR}$-specific shRNA" includes reference to one or more p75$^{NTR}$-specific shRNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions for regulating glucose metabolism. The compositions provide for reduced levels of p75$^{NTR}$ and/or reduced binding of p75$^{NTR}$ to a GTPase such as Rab31 or Rab5. The compositions are useful in methods of regulating glucose metabolism, which methods are also provided.

p75$^{NTR}$-Derived Peptides

The present disclosure provides p75$^{NTR}$-derived peptides that exhibit one or more of the following activities: 1) reduces binding of full-length p75$^{NTR}$ to Rab5 GTPase; 2) reduces binding of full-length p75$^{NTR}$ to Rab31 GTPase; 3) increases glucose disposal rate (GDR); 4) increases the insulin-stimulated GDR; 5) increases insulin-stimulated uptake of glucose into adipocytes and myocytes; 6) increases GLUT4 trafficking, e.g., increases GLUT4 translocation to the plasma membrane, e.g., in adipocytes and myocytes; 7) increases insulin sensitivity.

In some cases, a p75$^{NTR}$-derived peptide enhances glucose uptake into a cell, e.g., in some cases, a p75$^{NTR}$-derived peptide increases insulin-stimulated uptake of glucose into an adipocyte and/or a myocyte. For example, in some embodiments, a subject p75$^{NTR}$-derived peptide increases insulin-stimulated uptake of glucose into an adipocyte and/or a myocyte by at least about 15%, at least about 20%, at least about 25%, at least about 30%, at least about 50%, at least about 75%, at least about 2-fold, at least about 5-fold, at least about 10-fold, or more than 10-fold, compared to the insulin-stimulated uptake of glucose into the adipocyte or myocyte in the absence of the p75$^{NTR}$-derived peptide.

In some instances, a subject p75$^{NTR}$-derived peptide can increase glucose uptake into an adipocyte and/or a myocyte with an EC$_{50}$ in the range of from about 0.0001 nM to 100 µM (e.g., from about 0.0001 nM to about 0.001 nM, from about 0.001 nM to about 0.01 nM, from about 0.01 nM to about 0.1 nM, from about 0.1 nM to about 1 nM, from about 1 nM to about 10 nM, from about 10 nM to about 100 nM, from about 100 nM to about 1 µM, from about 1 µM to about 10 µM, or from about 10 µM to about 100 µM) in an in vitro assay for glucose uptake.

In some cases, a p75$^{NTR}$-derived peptide has a length of from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, from about 75 amino acids to about 80 amino acids, from about 80 amino acids to about 85 amino acids, from about 85 amino acids to about 90 amino acids, from about 90 amino acids to about 95 amino acids, or from about 95 amino acids to about 100 amino acids.

In some embodiments, a p75$^{NTR}$-derived peptide has a length of from about 15 amino acids to about 100 amino acids, as set out above, and has at least about 90%, at least about 95%, at least about 97%, at least about 98%, at least about 99%, or 100%, amino acid sequence identity with a contiguous stretch of from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, from about 75 amino acids to about 80 amino acids, from about 80 amino acids to about 85 amino acids, from about 85 amino acids to about 90 amino acids, or from about 90 amino acids to 92 amino acids or 95 amino acids, of an amino acid sequence depicted in FIG. 12, i.e., one of SEQ ID NOs:46-50.

In some cases, a p75$^{NTR}$-derived peptide comprises one of the following amino acid sequences:
a) LLASWATQDSATLDA (SEQ ID NO:1);
b) X$_1$LASWATQDSATLDA (SEQ ID NO:2);
c) LX$_1$ASWATQDSATLDA (SEQ ID NO:3);
d) LLX$_1$SWATQDSATLDA (SEQ ID NO:4);
e) LLAX$_1$WATQDSATLDA (SEQ ID NO:5);
f) LLASX$_1$ATQDSATLDA (SEQ ID NO:6);
g) LLASWX$_1$TQDSATLDA (SEQ ID NO:7);
h) LLASWAX$_1$QDSATLDA (SEQ ID NO:8);
i) LLASWATX$_1$DSATLDA (SEQ ID NO:9);
j) LLASWATQX$_1$SATLDA (SEQ ID NO:10);
k) LLASWATQDX$_1$ATLDA (SEQ ID NO: 11);
l) LLASWATQDSX$_1$TLDA (SEQ ID NO:12);
m) LLASWATQDSAX$_1$LDA (SEQ ID NO:13);
n) LLASWATQDSATX$_1$DA (SEQ ID NO:14);
o) LLASWATQDSATLX$_1$A (SEQ ID NO:15); and
p) LLASWATQDSATLDX$_1$ (SEQ ID NO:16),
where the peptide has a length of from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, or from about 50 amino acids to about 100 amino acids; and where X$_1$ is any amino acid.

Rab31-Derived Peptides

The present disclosure provides Rab31-derived peptides that exhibit one or more of the following activities: 1) reduces binding of full-length p75$^{NTR}$ to Rab31 GTPase; 2) increases glucose disposal rate (GDR); 3) increases the insulin-stimulated GDR; 4) increases insulin-stimulated uptake of glucose into adipocytes and myocytes; 5) increases GLUT4 trafficking, e.g., increases GLUT4 translocation to the plasma membrane, e.g., in adipocytes and myocytes; 6) increases insulin sensitivity.

In some cases, a Rab31-derived peptide enhances glucose uptake into a cell, e.g., in some cases, a Rab31-derived peptide increases insulin-stimulated uptake of glucose into an adipocyte and/or a myocyte. For example, in some embodiments, a subject Rab31-derived peptide increases insulin-stimulated uptake of glucose into an adipocyte and/or a myocyte by at least about 15%, at least about 20%, at least about 25%, at least about 30%, at least about 50%, at least about 75%, at least about 2-fold, at least about 5-fold, at least about 10-fold, or more than 10-fold, compared to the insulin-stimulated uptake of glucose into the adipocyte or myocyte in the absence of the Rab31-derived peptide.

In some instances, a subject Rab31-derived peptide can increase glucose uptake into an adipocyte and/or a myocyte with an EC$_{50}$ in the range of from about 0.0001 nM to 100 µM (e.g., from about 0.0001 nM to about 0.001 nM, from about 0.001 nM to about 0.01 nM, from about 0.01 nM to about 0.1 nM, from about 0.1 nM to about 1 nM, from about 1 nM to about 10 nM, from about 10 nM to about 100 nM, from about 100 nM to about 1 µM, from about 1 µM to about 10 µM, or from about 10 µM to about 100 µM) in an in vitro assay for glucose uptake.

In some cases, a Rab31-derived peptide comprises one of the following amino acid sequences:

| | |
|---|---|
| EHGPENIVMAIAGNK; | (SEQ ID NO: 17) |
| EX$_1$GPENIVMAIAGNK; | (SEQ ID NO: 18) |
| EHX$_1$PENIVMAIAGNK; | (SEQ ID NO: 19) |
| EHGX$_1$ENIVMAIAGNK; | (SEQ ID NO: 20) |
| EHGPX$_1$NIVMAIAGNK; | (SEQ ID NO: 21) |
| EHGPX$_1$NIVMAIAGNK; | (SEQ ID NO: 22) |
| EHGPEX$_1$IVMAIAGNK; | (SEQ ID NO: 23) |
| EHGPENX$_1$VMAIAGNK; | (SEQ ID NO: 24) |
| EHGPENIX$_1$MAIAGNK; | (SEQ ID NO: 25) |
| EHGPENIVX$_1$AIAGNK; | (SEQ ID NO: 26) |
| EHGPENIVMX$_1$IAGNK; | (SEQ ID NO: 27) |
| EHGPENIVMAX$_1$AGNK; | (SEQ ID NO: 28) |
| EHGPENIVMAIX$_1$GNK; | (SEQ ID NO: 29) |
| EHGPENIVMAIAX$_1$NK; | (SEQ ID NO: 30) |
| EHGPENIVMAIAGX$_1$K; and | (SEQ ID NO: 31) |
| EHGPENIVMAIAGNX$_1$, | (SEQ ID NO: 32) | where the peptide has a length of from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, or from about 50 amino acids to about 100 amino acids; and where $X_1$ is any amino acid.

Amide Bond Substitutions

In some cases, a peptide of the present disclosure (e.g., a $p75^{NTR}$-derived peptide; a Rab31-derived peptide) includes one or more linkages other than peptide bonds, e.g., at least two adjacent amino acids are joined via a linkage other than an amide bond. For example, to reduce or eliminate undesired proteolysis or other degradation pathways and/or to increase serum stability and/or to restrict or increase conformational flexibility, one or more amide bonds within the backbone of a $p75^{NTR}$-derived peptide or a Rab31-derived peptide can be substituted.

For example, one or more amide linkages (—CO—NH—) in a $p75^{NTR}$-derived peptide or a Rab31-derived peptide can be replaced with another linkage which is an isostere such as: —CH$_2$NH—, CH$_2$S—, —CH$_2$CH$_2$—, —CH=CH— (cis and trans), —COCH$_2$—, —CH(OH)CH$_2$— and —CH$_2$SO—. This replacement can be made by methods known in the art.

As another example, one or more amide linkages in a $p75^{NTR}$-derived peptide or a Rab31-derived peptide can be replaced with a reduced isostere pseudopeptide bond. Couder et al. (1993) *Int. J. Peptide Protein Res.* 41:181-184.

Amino Acid Substitutions

One or more amino acid substitutions can be made in a $p75^{NTR}$-derived peptide or a Rab31-derived peptide. The following are non-limiting examples:

a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a $p75^{NTR}$-derived peptide or a Rab31-derived peptide comprises one or more naturally occurring non-genetically encoded L-amino acids, synthetic L-amino acids or D-enantiomers of an amino acid. For example, a $p75^{NTR}$-derived peptide or a Rab31-derived peptide can comprise only D-amino acids. For example, a $p75^{NTR}$-derived peptide or a Rab31-derived peptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Other Modifications

A cysteine residue or a cysteine analog can be introduced into a $p75^{NTR}$-derived peptide or a Rab31-derived peptide to provide for linkage to another peptide via a disulfide linkage or to provide for cyclization of the $p75^{NTR}$-derived peptide or Rab31-derived peptide. Methods of introducing a cysteine or cysteine analog are known in the art; see, e.g., U.S. Pat. No. 8,067,532.

A $p75^{NTR}$-derived peptide or a Rab31-derived peptide can be cyclized. One or more cysteine or cysteine analogs can be introduced into a $p75^{NTR}$-derived peptide or a Rab31-derived peptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —(CH$_2$)$_n$—CO— or —(CH$_2$)$_n$—C$_6$H$_4$—CO—) with functional groups which allow for the introduction of a bridge. Some examples are disulfides, disulfide mimetics such as the —(CH$_2$)$_n$— carba bridge, thioacetal, thioether bridges (cystathionine or lanthionine) and bridges containing esters and ethers.

Other modifications include, for example, an N-alkyl (or aryl) substitution (ψ[CONR]), or backbone crosslinking to construct lactams and other cyclic structures. Other suitable derivatives of a peptide agent of the present disclosure include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a p75$^{NTR}$-derived peptide or a Rab31-derived peptide is replaced with a D-amino acid.

In some cases, a p75$^{NTR}$-derived peptide or a Rab31-derived peptide is a retroinverso analog. Sela and Zisman (1997) FASEB J. 11:449. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

A p75$^{NTR}$-derived peptide or a Rab31-derived peptide can include a protein transduction domain. "Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a p75$^{NTR}$-derived peptide or a Rab31-derived peptide. In some embodiments, a PTD is covalently linked to the carboxyl terminus of a p75$^{NTR}$-derived peptide or a Rab31-derived peptide. Exemplary protein transduction domains include but are not limited to a minimal undecapeptide protein transduction domain (corresponding to residues 47-57 of HIV-1 TAT comprising YGRKKRRQRRR (SEQ ID NO:36); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:37); Transportan GWTLNSAGYLLGKINLKALAALAKKIL (SEQ ID NO:38); KALAWEAKLAKALAKALAKHLAKALAKALKCEA (SEQ ID NO:39); and RQIKIWFQNRRMKWKK (SEQ ID NO:40). Exemplary PTDs include but are not limited to, YGRKKRRQRRR (SEQ ID NO:36), RKKRRQRRR (SEQ ID NO:41); an arginine homopolymer of from 3 arginine residues to 50 arginine residues; Exemplary PTD domain amino acid sequences include, but are not limited to, any of the following:

| | |
|---|---|
| YGRKKRRQRRR; | (SEQ ID NO: 36) |
| RKKRRQRRR; | (SEQ ID NO: 41) |
| YARAAARQARA; | (SEQ ID NO: 42) |
| THRLPRRRRRR; and | (SEQ ID NO: 43) |
| GGRRARRRRRR. | (SEQ ID NO: 44) |

A subject p75NTR-derived peptide or a subject Rab31-derived peptide can be modified by the covalent attachment of a water-soluble polymer such as poly(ethylene glycol) (PEG), copolymers of PEG and polypropylene glycol, polyvinylpyrrolidone or polyproline, carboxymethyl cellulose, dextran, polyvinyl alcohol, and the like. Such modifications also may increase the compound's solubility in aqueous solution. Polymers such as PEG may be covalently attached to one or more reactive amino residues, sulfhydryl residues or carboxyl residues. Numerous activated forms of PEG have been described, including active esters of carboxylic acid or carbonate derivatives, particularly those in which the leaving groups are N-hydroxsuccinimide, p-nitrophenol, imdazole or 1-hydroxy-2-nitrobenzene-3 sulfone for reaction with amino groups, multimode or halo acetyl derivatives for reaction with sulfhydryl groups, and amino hydrazine or hydrazide derivatives for reaction with carbohydrate groups.

Methods of Regulating Glucose Metabolism

The present disclosure provides methods of regulating glucose metabolism. A subject method generally involves administering to an individual an effective amount of an agent that reduces the level of p75$^{NTR}$ and/or reduces binding of p75$^{NTR}$ to a Rab5 or a Rab31 GTPase. A subject method can provide for one or more of: 1) increasing GDR; 2) increasing IS-GDR; 3) increasing insulin-stimulated glucose uptake into adipocytes and myocytes; 4) reducing blood glucose level; and 5) increasing insulin sensitivity. Suitable agents include a subject p75$^{NTR}$-derived peptide (as described above); a subject Rab31-derived peptide (as described above); and an interfering nucleic acid that reduces the level of p75$^{NTR}$ in a cell (as described below).

In some cases, an "effective amount" of an agent that reduces the level of p75$^{NTR}$ and/or reduces binding of p75$^{NTR}$ to a Rab5 or a Rab31 GTPase reduces a blood glucose level in an individual in need thereof by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75%, compared to the blood glucose level in the individual in the absence of treatment with the agent.

In some cases, an "effective amount" of an agent that reduces the level of p75$^{NTR}$ and/or reduces binding of p75$^{NTR}$ to a Rab5 or a Rab31 GTPase increases the GDR or the IS-GDR in an individual in need thereof by at least about 10%, at least about 25%, at least about 50%, at least about 75%, at least about 2-fold, at least about 5-fold, or more than 5-fold, compared to the GDR or the IS-GDR in the individual in the absence of treatment with the agent.

In some cases, an "effective amount" of an agent that reduces the level of p75$^{NTR}$ and/or reduces binding of p75$^{NTR}$ to a Rab5 or a Rab31 GTPase increases insulin sensitivity an individual in need thereof by at least about 10%, at least about 25%, at least about 50%, at least about 75%, at least about 2-fold, at least about 5-fold, or more than 5-fold, compared to the insulin sensitivity in the individual in the absence of treatment with the agent.

Interfering RNA

An agent that reduces the level of p75$^{NTR}$ includes an interfering nucleic acid specific for p75$^{NTR}$ (including a nucleic acid comprising a nucleotide sequence encoding an interfering nucleic acid specific for p75$^{NTR}$).

An interfering nucleic acid specific for p75$^{NTR}$ can reduce the level of p75$^{NTR}$ in a cell (e.g., an adipocyte; a myocyte) by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75%, compared to the level of p75$^{NTR}$ in the cell in the absence of the interfering nucleic acid.

An interfering nucleic acid specific for p75$^{NTR}$ can reduces a blood glucose level in an individual in need thereof by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75%, compared to the blood glucose level in the individual not treated with the interfering nucleic acid.

In some cases, an interfering nucleic acid specific for p75$^{NTR}$ is an shRNA, or a nucleic acid comprising a nucleotide sequence encoding an shRNA specific for p75$^{NTR}$. In some cases a nucleotide sequence encoding an shRNA specific for p75$^{NTR}$ is operably linked to a control element (e.g., a promoter and/or an enhancer) that provides for selective expression in an adipocyte. In some cases a nucleotide sequence encoding an shRNA specific for p75$^{NTR}$ is operably linked to a control element (e.g., a promoter and/or an enhancer) that provides for selective expression in myocyte (muscle cell).

In some cases, a control element (e.g., a promoter and/or an enhancer) that provides for selective expression in a myocyte is a smooth muscle cell-specific control element. Smooth muscle cell-specific control elements include, e.g., a SM22α promoter (see, e.g., Akyürek et al. (2000) Mol. Med. 6:983; and U.S. Pat. No. 7,169,874); a smoothelin promoter (see, e.g., WO 2001/018048); an α-smooth muscle actin promoter; etc. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

In some cases, a promoter that provides for selective expression in a myocyte is a skeletal muscle cell-specific control element (e.g., promoter and/or enhancer). Skeletal muscle cell-specific promoters include, but are not limited to, a Pitx3 promoter (Coulon et al. (2007) J. Biol. Chem. 282:33192); a Mef2c promoter (see, e.g., Heidt and Black (2005) Genesis 42:28); a desmin control element (see, e.g., Pacak et al. (2008) Genetic Vaccines and Therapy 6:13; and Talbot et al. (2010) Mol. Ther. 18:601); a pM or a pH control element from a human aldolase gene (see, e.g., Concordet et al. (1993) Mol. Cell. Biol. 13:9); cardiac troponin T gene promoter (see, e.g, Mar and Ordahl (1988) Proc. Natl. Acad. Sci. USA 85:6404); a muscle creatine kinase control element (see, e.g., Wang et al. (2008) Gene Ther. 15:1489); a skeletal α-actin control element (Ernst et al. (1991) Mol. Cell Biol. 11:3735); and the like.

Adipocyte-specific control elements can include, e.g., an aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139:1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Agents that reduce the level of p75$^{NTR}$ in a cell (e.g., in an adipocyte; in a myocyte) include nucleic acid agents ("inhibitory nucleic acids") that reduce the level of active of p75$^{NTR}$ in a cell. Suitable agents that reduce the level of p75$^{NTR}$ activity in a cell (e.g., that reduce the total amount of p75$^{NTR}$ in a cell) include interfering nucleic acids, e.g., interfering RNA molecules. In one embodiment, reduction of p75$^{NTR}$ levels is accomplished through RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), or a short hairpin RNA (shRNA) molecule, or modulation of expression of a small interfering RNA (siRNA) so as to provide for decreased levels of p75$^{NTR}$.

p75$^{NTR}$-specific interfering nucleic acids can be designed based on the nucleotide sequence of a p75NTR-encoding nucleotide sequence. For example, in some embodiments, a p75NTR-encoding nucleotide sequence as set forth in FIG. 15 is used to design an interfering nucleic acid.

The term "short interfering nucleic acid," "siNA," "short interfering RNA," "siRNA," "short interfering nucleic acid molecule," "short interfering oligonucleotide molecule," or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6):509-16; Xie et al. Drug Discov Today. 2006 January; 11(1-2):67-73; Grunweller et al. Curr Med. Chem. 2005; 12(26):3143-61; and Pekaraik et al. Brain Res Bull. 2005 Dec. 15; 68(1-2):115-20.

Methods for design and production of siRNAs to a desired target are known in the art, and their application to p75NTR genes for the purposes disclosed herein will be readily apparent to the ordinarily skilled artisan, as are methods of production of p75NTR having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which is incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32(Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

A suitable siRNA or shRNA sequence for reducing $p75^{NTR}$ expression includes, e.g., 5'-GGAGACAUGUUC-CACAGGCAUCGAAAUGCCUGUGGAACAUGUCUC-CUU-3' (shRNA) (SEQ ID NO:56).

siNA molecules can be of any of a variety of forms. For example the siNA can be a double-stranded polynucleotide molecule comprising self-complementary sense and antisense regions, wherein the antisense region comprises a nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 base pairs to about 30 base pairs, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 nucleotides to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules lack 2'-hydroxy (2'-OH) containing nucleotides. siNAs do not necessarily require the presence of nucleotides having a 2'-hydroxy group for mediating RNAi and as such, siNA molecules optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules can be used to epigenetically silence a target gene at the post-transcriptional level, the pre-transcriptional level, or both the post-transcriptional and pre-transcriptional levels. In a non-limiting example, epigenetic regulation of gene expression by siNA molecules can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819;

Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of p75NTR.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Formulations, Dosages, and Routes of Administration

A p75$^{NTR}$-derived peptide, or a Rab31-derived peptide, or a p75$^{NTR}$-specific interfering RNA can be formulated with one or more pharmaceutically acceptable excipients. p75$^{NTR}$-derived peptides, Rab31-derived peptides, and p75$^{NTR}$-specific interfering RNAs are referred to generically below as "active agent" or "drug." Thus, the present disclosure provides a pharmaceutical composition comprising: a) a subject p75$^{NTR}$-derived peptide; and b) a pharmaceutically acceptable excipient. The present disclosure further provides a pharmaceutical composition comprising: a) a p75$^{NTR}$-specific interfering RNA (including a nucleic acid comprising a nucleotide sequence encoding a p75$^{NTR}$-specific interfering RNA); and b) a pharmaceutically acceptable excipient. The present disclosure further provides a pharmaceutical composition comprising: a) a Rab31-derived peptide; and b) a pharmaceutically acceptable excipient.

A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for an active agent depend on the particular compound employed and the effect to be achieved, and the pharmacodynamics associated with each compound in the host.

In the subject methods, a p75$^{NTR}$-derived peptide, or a Rab31-derived peptide, or a p75$^{NTR}$-specific interfering RNA may be administered to the host using any convenient means capable of resulting in the desired outcome, e.g., reduction of disease, reduction of a symptom of a disease, reduction of blood glucose levels, etc. Thus, a p75$^{NTR}$-derived peptide, a Rab31-derived peptide, or a p75$^{NTR}$-specific interfering RNA can be incorporated into a variety of formulations for therapeutic administration. More particularly, a p75$^{NTR}$-derived peptide, a Rab31-derived peptide, or a p75$^{NTR}$-specific interfering RNA can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, a p75$^{NTR}$-derived peptide, a Rab31-derived peptide, or a p75$^{NTR}$-specific interfering RNA ("active agent") may be administered in the form of its pharmaceutically acceptable salts, or an active agent may be used alone or in appropriate association, as well as in combination, with other pharmaceutically active compounds. The following methods and excipients are merely exemplary and are in no way limiting.

For oral preparations, an active agent (a p75$^{NTR}$-derived peptide, a Rab31-derived peptide, or a p75$^{NTR}$-specific interfering RNA) can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

An active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, an active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the active agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug ("active agent") is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (a $p75^{NTR}$-derived peptide, a Rab31-derived peptide, or a $p75^{NTR}$-specific interfering RNA) is delivered using an implantable drug delivery system, e.g., a system that is programmable to provide for administration of an active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for use is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of an active agent adequate to achieve the desired state in the subject being treated.

Oral Formulations

In some embodiments, an active agent (a $p75^{NTR}$-derived peptide, a Rab31-derived peptide, or a $p75^{NTR}$-specific interfering RNA) is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HP-MCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include an active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent, and an active agent (e.g., a $p75^{NTR}$-derived peptide or a $p75^{NTR}$-specific interfering RNA). Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Inhalational Formulations

An active agent (a $p75^{NTR}$-derived peptide, a Rab31-derived peptide, or a $p75^{NTR}$-specific interfering RNA) will in some embodiments be administered to a patient by means of a pharmaceutical delivery system for the inhalation route. An active agent can be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. A system that depends on the power of a compressed gas to expel the active agent from a container can be used. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed for use herein are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing the active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment of the present disclosure can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present disclosure. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. No. 5,775,320 and U.S. Pat. No. 5,740,794.

Dosages and Dosing

Depending on the subject and condition being treated and on the administration route, an active agent (a $p75^{NTR}$- derived peptide, a Rab31-derived peptide, or a $p75^{NTR}$-specific interfering RNA) can be administered in dosages of, for example, 0.1 µg to 500 mg/kg body weight per day, e.g., from about 0.1 µg/kg body weight per day to about 1 µg/kg body weight per day, from about 1 µg/kg body weight per day to about 25 µg/kg body weight per day, from about 25 µg/kg body weight per day to about 50 µg/kg body weight per day, from about 50 µg/kg body weight per day to about 100 µg/kg body weight per day, from about 100 µg/kg body weight per day to about 500 µg/kg body weight per day, from about 500 µg/kg body weight per day to about 1 mg/kg body weight per day, from about 1 mg/kg body weight per day to about 25 mg/kg body weight per day, from about 25 mg/kg body weight per day to about 50 mg/kg body weight per day, from about 50 mg/kg body weight per day to about 100 mg/kg body weight per day, from about 100 mg/kg body weight per day to about 250 mg/kg body weight per day, or from about 250 mg/kg body weight per day to about 500 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, an active agent can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active agent, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of active agent in a blood sample taken from the individual being treated, about 24 hours after administration of the active agent to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

In some embodiments, multiple doses of an active agent are administered. The frequency of administration of an active agent can vary depending on any of a variety of factors, e.g., severity of the symptoms, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, an active agent is administered continuously.

The duration of administration of an active agent, e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, an active agent is administered for the lifetime of the individual.

Routes of Administration

An active agent (a $p75^{NTR}$-derived peptide, a Rab31-derived peptide, or a $p75^{NTR}$-specific interfering RNA) is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, ocular (e.g., topically to the eye, intravitreal, etc.), rectal, nasal, oral, and other enteral and parenteral routes of administration. Routes of administration may be combined, if desired, or adjusted depending upon the agent and/or the desired effect. The active agent can be administered in a single dose or in multiple doses.

An active agent can be administered to a host using any available conventional methods and routes suitable for delivery of conventional drugs, including systemic or localized routes. In general, suitable routes of administration include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

Methods of administration of an active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Subjects Suitable for Treatment

The phrase "glucose metabolism disorder" encompasses any disorder characterized by a clinical symptom or a combination of clinical symptoms that are associated with an elevated level of glucose and/or an elevated level of insulin in a subject relative to a healthy individual. Elevated levels of glucose and/or insulin may be manifested in the following disorders and/or conditions: type II diabetes (e.g. insulin-resistance diabetes), gestational diabetes, insulin resistance, impaired glucose tolerance, hyperinsulinemia, impaired glucose metabolism, pre-diabetes, metabolic disorders (such as metabolic syndrome which is also referred to as syndrome X), obesity, obesity-related disorder; type I diabetes, idiopathic type 1 diabetes, latent autoimmune diabetes in adults, early-onset type 2 diabetes, youth-onset atypical diabetes, maturity onset diabetes of the young, malnutrition-related diabetes, and gestational diabetes.

An example of a suitable patient may be one who is hyperglycemic and/or hyperinsulinemic and who is also diagnosed with diabetes mellitus (e.g. Type II diabetes). "Diabetes" refers to a progressive disease of carbohydrate metabolism involving inadequate production or utilization of insulin and is characterized by hyperglycemia and glycosuria.

"Hyperglycemia", as used herein, is a condition in which an elevated amount of glucose circulates in the blood plasma relative to a healthy individual and can be diagnosed using methods known in the art. For example, hyperglycemia can be diagnosed as having a fasting blood glucose level between 5.6 to 7 mM (pre-diabetes), or greater than 7 mM (diabetes).

"Hyperinsulinemia", as used herein, is a condition in which there are elevated levels of circulating insulin while blood glucose levels may either be elevated or remain normal. Hyperinsulinemia can be caused by insulin resistance which is associated with dyslipidemia such as high triglycerides, high cholesterol, high low-density lipoprotein (LDL) and low high-density lipoprotein (HDL), high uric acids, polycystic ovary syndrome, type II diabetes and obesity. Hyperinsulinemia can be diagnosed as having a plasma insulin level higher than about 2 µU/mL.

A patient having any of the above disorders may be a suitable candidate in need of a therapy in accordance with the present method so as to receive treatment for hyperglycemia, hyperinsulinemia, and/or glucose intolerance. Administering the subject protein in such an individual can restore glucose homeostasis and may also decrease one or more of symptoms associated with the disorder.

Candidates for treatment using the subject method may be determined using diagnostic methods known in the art, e.g. by assaying plasma glucose and/or insulin levels. Candidates for treatment include those who have exhibited or are exhibiting higher than normal levels of plasma glucose/ insulin. Such patients include patients who have a fasting blood glucose concentration (where the test is performed after 8 to 10 hour fast) of higher than about 100 mg/dL, e.g., higher than about 110 mg/dL, higher than about 120 mg/dL, about 150 mg/dL up to about 200 mg/dL or more. Individuals suitable to be treated also include those who have a 2 hour postprandial blood glucose concentration or a concentration after a glucose tolerance test (e.g. 2 hours after ingestion of a glucose-rich drink), in which the concentration is higher than about 140 mg/dL, e.g., higher than about 150 mg/dL up to 200 mg/dL or more. Glucose concentration may also be presented in the units of mmol/L, which can be acquired by dividing mg/dL by a factor of 18.

Screening Methods

The present disclosure provides methods for identifying a candidate agent for reducing blood glucose levels and/or increasing insulin sensitivity in an individual. A subject screening method generally involves: a) contacting a polypeptide comprising an intracellular domain of a $p75^{NTR}$ (e.g., a $p75^{NTR}$ ICD polypeptide) with: i) a GTPase selected from Rab31 and Rab5; and ii) a test agent; and b) determining the effect of the test agent on binding of the intracellular domain of $p75^{NTR}$ to Rab31 or Rab5. In some cases, a subject screening method is a cell-free in vitro assay. In other cases, a subject screening method is a cell-based in vitro assay. For example, a subject method can comprise: a) contacting in a reaction mixture: i) a polypeptide comprising an intracellular domain of a $p75^{NTR}$ (e.g., a $p75^{NTR}$ ICD polypeptide); ii) a GTPase selected from Rab31 and Rab5; and iii) a test agent; and b) determining the effect of the test agent on binding of the intracellular domain of $p75^{NTR}$ to Rab31 or Rab5.

In some cases, the polypeptide comprising an intracellular domain of a $p75^{NTR}$ (e.g., a $p75^{NTR}$ ICD polypeptide) is immobilized. In other cases, the GTPase is immobilized. In some cases, the Rab31 GTPase polypeptide is a subject Rab31-derived peptide.

A test agent that inhibits binding of the intracellular domain of $p75^{NTR}$ to Rab31 or Rab5 is considered a candidate agent for reducing blood glucose levels and/or increasing insulin sensitivity. For example, a test agent that inhibits binding of the intracellular domain of $p75^{NTR}$ to Rab31 or Rab5 by at least about 15%, at least about 20%, at least about 25%, at least about 30%, at least about 35%, at least about 40%, at least about 50%, at least about 60%, at least about 70%, or more than 70%, is considered a candidate agent for reducing blood glucose levels and/or increasing insulin sensitivity.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the present disclosure include controls, where suitable controls include a sample (e.g., a sample comprising a $p75^{NTR}$ ICD polypeptide, and a Rab5 or Rab31 polypeptide, in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents such as salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, e.g., between 4° C. and 40° C. Incubation periods are selected for optimum activity, but may also be optimized to facilitate rapid high-throughput screening. Typically between 0.1 hour and 1 hour will be sufficient.

In some embodiments, a test compound of interest has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

A candidate agent can be assessed for any cytotoxic activity it may exhibit toward a living cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

Whether a test agent reduces $p75^{NTR}$ ICD polypeptide binding to a Rab5 or Rab31 polypeptide can be determined using any assay method suitable for determining protein-protein binding. Such assays include, e.g., enzyme-linked immunosorbent assays (ELISA); bioluminescence resonance energy transfer (BRET) assays; Förster resonance energy transfer (FRET) assays; immunoprecipitation assays; protein blot assays; radioimmunoassays; and the like.

In many embodiments, the screening method is carried out in vitro, in a cell-free assay. In some embodiments, the in vitro cell-free assay will employ a purified $p75^{NTR}$ ICD polypeptide, where "purified" refers to free of contaminants or any other undesired components. Purified $p75^{NTR}$ ICD polypeptide that is suitable for a subject screening method is at least about 50% pure, at least about 60% pure, at least about 70% pure, at least about 75% pure, at least about 80% pure, at least about 85% pure, at least about 90% pure, at least about 95% pure, at least about 98% pure, at least about 99% pure, or greater than 99% pure. Similarly the Rab5 or Rab31 polypeptide can be purified.

Purified $p75^{NTR}$ ICD polypeptide, and/or purified Rab5 or Rab31 polypeptide, will in some embodiments be stabilized by addition of one or more stabilizing agents, to maintain enzymatic activity. In some embodiments, a solution of purified $p75^{NTR}$ ICD polypeptide, and/or purified Rab5 or Rab31 polypeptide, comprises an aqueous solution comprising such polypeptide and from about 10% to about 50% glycerol, e.g., from about 10% to about 15%, from about 15% to about 20%, from about 20% to about 25%, from about 25% to about 30%, from about 30% to about 35%, from about 35% to about 40%, from about 40% to about 45%, or from about 45% to about 50% glycerol. In some embodiments, a solution comprising a $p75^{NTR}$ ICD polypeptide, and/or purified Rab5 or Rab31 polypeptide, further comprises one or more of a chelating agent (e.g., EDTA or EGTA); salts such as NaCl, $MgCl_2$, KCl, and the like; buffers, such as a Tris buffer, phosphate-buffered saline, sodium pyrophosphate buffer, and the like; one or more protease inhibitors; and the like.

A $p75^{NTR}$ ICD polypeptide suitable for use in a subject screening method has a length of from about 15 amino acids to about 100 amino acids, as set out above, and has at least about 90%, at least about 95%, at least about 97%, at least about 98%, at least about 99%, or 100%, amino acid sequence identity with a contiguous stretch of from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, from about 75 amino acids to about 80 amino acids, from about 80 amino acids to about 85 amino acids, from about 85 amino acids to about 90 amino acids, or from about 90 amino acids to 92 amino acids or 95 amino acids, of an amino acid sequence depicted in FIG. 12 (i.e., one of SEQ ID NOs:46-50).

In some cases, the intracellular domain (ICD) of $p75^{NTR}$ comprises the amino acid sequence LLASWATQDSATLDA (SEQ ID NO:1), or an amino acid sequence differing by no more than 1, 2, 3, 4, or 5 amino acids from LLASWATQD-SATLDA (SEQ ID NO:1), as long as the p75$^{NTR}$ ICD polypeptide can bind to the Rab5 or Rab31 polypeptide.

A Rab5 polypeptide suitable for use in a subject screening method comprises an amino acid sequence having least about 75%, at least about 85%, at least about 90%, at least about 95%, at least about 98%, at least about 99%, or 100%, amino acid sequence identity with a contiguous stretch of from about 150 amino acids to about 200 amino acids, or from about 200 amino acids to about 215 amino acids, of the amino acid sequence depicted in FIG. 13 (SEQ ID NO:51).

A Rab31 polypeptide suitable for use in a subject screening method comprises an amino acid sequence having least about 75%, at least about 85%, at least about 90%, at least about 95%, at least about 98%, at least about 99%, or 100%, amino acid sequence identity with a contiguous stretch of from about 125 amino acids to about 150 amino acids, from about 150 amino acids to about 175 amino acids, or from about 175 amino acids to about 195 amino acids, with the amino acid sequence depicted in FIG. 14 (SEQ ID NO:52).

In some embodiments, a subject assay will employ a fusion protein, comprising a p75$^{NTR}$ ICD polypeptide fused in-frame to a fusion partner. In some embodiments, the fusion partner is attached to the amino terminus of the p75$^{NTR}$ ICD polypeptide. In other embodiments, the fusion partner is attached to the carboxyl terminus of the p75$^{NTR}$ ICD polypeptide. In other embodiments, the fusion partner is fused in-frame to the p75$^{NTR}$ ICD polypeptide at a location internal to the p75$^{NTR}$ ICD polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., p75$^{NTR}$ ICD/6His), glutathione-S-transferase, and the like; polypeptides that provide for subcellular localization; and polypeptides that provide for secretion from a cell.

In some embodiments, the fusion partner is an epitope tag. In some embodiments, the fusion partner is a metal chelating peptide. In some embodiments, the metal chelating peptide is a histidine multimer, e.g., (His)$_6$. In some embodiments, a (His)$_6$ multimer is fused to the amino terminus of a p75$^{NTR}$ ICD polypeptide; in other embodiments, a (His)$_6$ multimer is fused to the carboxyl terminus of a p75$^{NTR}$ ICD polypeptide. The (His)$_6$-p75$^{NTR}$ ICD fusion protein is purified using any of a variety of available nickel affinity columns (e.g. His-bind resin, Novagen).

In some embodiments, a subject screening method is carried out in vitro in a cell, e.g., a cell grown in cell culture as a unicellular entity. Suitable cells include, e.g., eukaryotic cells, e.g., mammalian cells such as CHO cells 293 cells, 3R3 cells, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1 p75 Neurotrophin Receptor Regulates Glucose Homeostasis and Insulin Sensitivity

Materials and Methods

Mice.

p75$^{NTR-/-}$ mice (Lee et al. (1992) Cell 69:737-749) were obtained from Jackson Laboratory. Mice were on a C57BL/6 background and were further crossed to C57BL/6 background (11-12 crossings). Heterozygous p75$^{NTR+/-}$ were crossed to obtain p75$^{NTR-/-}$, p75$^{NTR+/-}$ and p75$^{NTR+/+}$ littermates used in experiments. Male mice were fed with standard chow and had access to food and water ad libitum. MRI experiments were carried out on a Varian 7T 300 MHz Horizontal Bore MRI System at the Department of Radiology & Biomedical Imaging at UCSF. Fat and lean tissue volumes were assessed by using the Volocity 3D Image Analysis Software (PerkinElmer). All animal study protocols were reviewed and approved by the Institutional Animal Care and Use Committee of the University of California San Francisco and San Diego and are in accordance with those set by the National Institutes of Health.

Glucose and Insulin Tolerance Tests.

Glucose and insulin tolerance tests (GTT and ITT) were performed on 6 h fasted mice. For GTT, animals were injected i.p. with dextrose (1 g/Kg, Hospira, Inc) whereas for ITT 0.4 units/Kg insulin (Novolin R, Novo-Nordisk) was injected i.p. Glucose excursion following injection was monitored over time. Blood samples were drawn at 0, 10, 30, 60 and 120 min after dextrose or insulin injection. Glucose was measured using a One-touch glucose-monitoring system (Lifescan).

Hyperinsulinemic-Euglycemic Clamp Studies.

Clamp studies were performed as previously described (2-4). Briefly, dual jugular catheters were implanted and mice were allowed to recover three days before clamp procedure. Following 6 h fast, an equilibrating solution (5.0 μCi/h, 0.12 ml/h [3-$^3$H]D-glucose, NEN Life Science Products) was infused into one of the jugular catheters for 90 min to equilibrate the plasma tracer. Following this equilibrating period, a basal blood sample was drawn via tail vein to obtain tracer counts for the calculation of basal glucose uptake. The insulin (8 mU/Kg/min, at a flow rate of 2 ml/min) plus tracer (0.5 μCi/h) infusion and glucose (50% dextrose, Abbot, variable rate) were initiated simultaneously, with the glucose flow rate adjusted to reach a steady state blood glucose concentration (~120 min). Steady state was confirmed by stable tracer counts in plasma during final 30 min of clamp. At the end of the clamp, a blood sample was taken at 110 and 120 min for the determination of tracer-specific activity. And at the steady state, the rate of glucose disappearance or the total glucose disposal rate (GDR) is equal to the sum of the rate of endogenous or hepatic glucose production (HGP) plus the exogenous glucose infusion rate (GIR). The insulin-stimulated glucose disposal rate (IS-GDR) is equal to the total GDR minus the basal glucose turnover rate.

Cell Culture and Primary Adipocyte Isolation.

3T3L1 cells were maintained in DMEM containing 10% bovine serum. All media were supplemented with 1% penicillin/streptomycin (Invitrogen). Mouse embryonic fibroblasts (MEFs) were isolated from wild-type (WT) and p75$^{NTR-/-}$ embryos as described (5). Briefly, heads and internal organs were removed from E12-14 embryos, and the remaining embryo was minced with scissors. Ten ml of ice cold phosphate-buffered saline (PBS) was added and minced embryos were centrifuged for 5 minutes at 500×g. Each embryo was resuspended in 7.5 ml Trypsin-EDTA for 20 minutes at 37° C. with occasional shaking. After trypsin deactivation by 7.5 ml DMEM with 10% FBS the suspension was poured through a 70 μm filter and cells were cultured in DMEM with 10% fetal bovine serum (FBS). Differentiation of 3T3L1 cells and MEFs was performed as described (6). Briefly, differentiation was induced by incubating confluent monolayers for 3 days in DMEM containing 10% fetal bovine serum (FBS), 0.5 mM 3-isobutyl-1-methylxanthine, 0.4 μg/ml dexamethasone, and 1 μg/ml of insulin. Medium was replaced every 2 days with DMEM containing 10% FBS. After 8-12 days, 75% of the cells expressed the adipocyte phenotype as assessed by Oil Red O. Isolation of primary adipocytes from epididymal fat pads was performed as described (7). Briefly, fat pads were minced in Krebs-Ringer Bicarbonate-Hepes (KRBH) buffer, pH 7.4, treated with collagenase (Invitrogen) for 40 min, filtered through a nylon strainer and centrifuged at 400×g for 1 minute. Fully-differentiated adipocytes were transfected by electroporation using Amaxa Cell Line Nucleofector kit L (Lonza) following manufacturer's instructions. For p75$^{NTR}$ knockdown experiments, 3T3L1 cells were differentiated for 6-8 days and infected with lentivirus encoding a short hairpin shRNA for mouse p75$^{NTR}$ (8) and L6 myocytes were transfected with siGENOME SMART pool for rat p75$^{NTR}$ (Thermo Scientific).

Glucose Uptake Assay.

Fully differentiated 3T3L1 adipocytes and eight day differentiated WT and p75$^{NTR-/-}$ MEFs were serum-starved for 3 hrs in DMEM and then equilibrated in Hepes/Salt (H/S) buffer for 30 min prior to treatment with 100 nM insulin for 30 min at 37° C. Thirty min after the addition of insulin, [$^3$H]-2-deoxyglucose (Amersham) and 2 mM 2-deoxyglucose (Sigma) in H/S buffer was added. After incubation at 37° C. for 10 min, the reactions were terminated by washing twice with ice-cold PBS. Cells were lysed in 1 M NaOH for 30 min at room temperature. An equal volume of 1 M HCl was added and incorporated radioactivity was measured by liquid scintillation counting. 3T3L1 adipocytes and WT and p75$^{NTR-/-}$ MEF-derived adipocytes were transfected by electroporation with green fluorescent protein (GFP), p75$^{NTR}$ FL, and p75$^{NTR}$ intracellular domain (ICD); and Rab5S34N and Rab31Q64L expression vectors were also used. For neurotrophin stimulation, 3T3L1 adipocytes were treated with 100 ng/ml of nerve growth factor (NGF) (Peprotech) or 50 ng/ml of brain-derived neurotrophic factor (BDNF) (Peprotech) for 1 h or 12 h before insulin stimulation. Measurement of glucose uptake in primary adipocytes was performed as described (9), after several washes with KRBH buffer, a 25-30% suspension of primary isolated adipocytes was incubated with KRBH buffer without glucose for 30 min prior to insulin stimulation. After insulin stimulation 0.1 mM [$^3$H]-2DG (Perkin Elmer) were added and incubated for 10 min. Immediately after incubation, the suspension was loaded on top of 0.2 ml of silicon oil in a 0.4 ml polyethylene tube and centrifuged. The fat cells were isolated and the level of radioactivity was counted. An aliquot of the suspension was used to determine protein concentration.

Cell Fractionation, Western Blotting and Antibodies.

For fractionation experiments, cells were washed twice with 20 mM Tris HCl/1 mM EDTA/255 mM sucrose, pH 7.4, then resuspended and homogenized with 10 strokes of a pestle. Cell lysates were centrifuged at 4° C. at 16000 g for 15 min. The pellet was resuspended in buffer, spun again, and the new pellet was resuspended in buffer, and was applied to a 1.12 M sucrose cushion containing 20 mM Tris HCl and 1 mM EDTA and centrifuged at 101,000×g for 70 min. Plasma membranes were collected from the interface and resuspended in buffer. Equal amounts of protein were then analyzed by Western blotting as described (8). Antibodies used were: mouse anti-Glut4, 1:1000, (Abcam); mouse anti-Glut1, 1:1000, (Abcam); rabbit anti-Ser 473 phospho-Akt, 1:1000, (Cell signaling); rabbit anti-Akt, 1:1000, (Cell signaling); mouse anti-Rab31, 1:1000, (Abnova); rabbit anti-Rab5, 1:1000, (Abcam); rabbit anti-myc, 1:1000, (Abcam); mouse anti-HA, 1:1000, (Cell Signaling); rabbit anti-GFP, 1:1000, (Santa Cruz Biotechnology); rabbit anti-p75$^{NTR}$ 9992, 1:2000; rabbit anti-p75$^{NTR}$, 1:1000 (Millipore); rabbit anti-Actin, 1:1000, (Sigma); rabbit anti-Gapdh, 1:3000, (Abcam). Quantification was performed on the Scion NIH Imaging Software.

Co-Immunoprecipitation (Co-IP).

Co-IP was performed as previously described (22). Briefly, cell lysates were prepared in 1% Nonidet P-40 (NP-40; non-ionic detergent), 200 mM NaCl, 1 mM EDTA, and 20 mM Tris-HCl, pH 8.0. Immunoprecipitations (IPs) were performed with an anti-p75$^{NTR}$ antibody and immunoblot with anti-Rab31 and anti-p75$^{NTR}$. For mapping experiments, myc-Rab31 cDNA was cotransfected with HA-tagged p75$^{NTR}$ deletion constructs into HEK293T cells. Immunoprecipitation (IP) was performed with an anti-myc antibody. Cell lysates were probed with an anti-hemagglutinin (anti-HA) or an anti-myc antibody. For co-IP experiments using recombinant proteins, equimolar amounts (1 μM) of purified recombinant glutathione-S transferase (GST), activated GST-Rab5, and p75$^{NTR}$ ICD were mixed in binding buffer (5% glycerol, 20 mM Tris-HCl pH=7.5, 100 mM NaCl, 10 mM EDTA, 0.025% Tween-20) and incubated for 1 hour at 4° C. To nucleotide load GST-Rab5 recombinant protein, GST-Rab5 was incubated with 5% glycerol, 20 mM Tris-HCl pH=7.5, 150 mM NaCl, 5 mM EDTA, containing 1 mM GTPγS at 30° C. for 30 min. The reaction was stopped by adding 60 mM MgCl$_2$. For inhibition experiments, 1 μM Tat-Pep5 (Calbiochem) or 1 μM control Tat-fused peptide (Calbiochem) were added for 1 h together with the recombinant p75ICD and activated GST-Rab5. Washed glutathione-sepharose beads were added according to the manufacturer's instructions for an additional hour. Beads were sedimented by centrifugation (10000×g for 1 min) and washed three times. Proteins associated with the beads were eluted by boiling in loading buffer and separated by sodium dodecyl sulfate-polyacrylamide gel electrophoresis (SDS-PAGE).

In Vitro GST Activity Assay.

The activity assay was performed as described (10) in serum-starved WT and p75$^{NTR-/-}$ MEF-derived adipocytes treated with insulin as indicated, 1 mg of GST-EEA1/ml PBS was incubated with 1 ml GSH sepharose beads for 1 h at 4° C. Beads were spun down, washed 10 times, and resuspended in PBS to create a 50% slurry. 2 mg of lysate in a final volume of 500 ml lysis buffer were immunoprecipitated with 50 μl of GST-EEA1-bound GSH sepharose bead slurry overnight at 4° C. to pull down the active forms of Rab5 and Rab31. Beads were spun down, washed, boiled in sodium dodecyl sulfate (SDS), and loaded on 8-12% Tris-Glycine gel and blotted for Rab5 or Rab31. Whole cell lysates taken before incubation with beads was used for Western blotting for Rab5, Rab31 and Actin.

Peptide Array Mapping.

Peptide arrays were manufactured by Kinexus Bioinformatics Corporation (Vancouver, Canada). Synthetic overlapping peptides (25 amino acids in length) for p75ICD were spotted on nitrocellulose membranes. Membranes were overlaid with 1 μg/ml recombinant GST-Rab31, GST-Rab5 and $p75^{NTR}$ ICD. Bound recombinant GST-Rab31 and GST-Rab5 were detected using rabbit anti-GST (1:1000, Cell Signaling) and bound recombinant p75ICD was detected using rabbit anti-$p75^{NTR}$ (1:1000, Millipore) followed by secondary anti-rabbit horseradish peroxidase antibody (1:5000, Cell Signaling).

Immunocytochemistry.

$p75^{NTR+/+}$ and $p75^{NTR-/-}$ MEFs-derived adipocytes were transfected by electroporation with the GFP-Glut4 expression vector. After 24 hours, adipocytes were serum starved for 2 hours in DMEM and stimulated with 100 nM insulin for 30 min, fixed with paraformaldehyde and analyzed. Fully differentiated 3T3L1 were fixed with paraformaldehyde, and stained using the following antibodies: rabbit anti-$p75^{NTR}$ (Millipore), mouse anti-Rab31 (Abnova) and rabbit anti-Rab5 (Abcam).

Microscopy and Image Acquisition.

Microscopic images were acquired with an Axioplan II epifluorescence microscope (Carl Zeiss, Inc.) and dry Plan-Neofluar objectives (10×0.3 NA, 20×0.5 NA, or 40×0.75 NA) using an Axiocam HRc CCD camera and the Axiovision image analysis software.

Statistical Analysis.

Data are shown as the means±SEM. Differences between groups were examined by unpaired Student's t test or by one-way ANOVA for multiple comparisons followed by Bonferroni's correction for comparison of means.

Results

Loss of $p75^{NTR}$ Increases Insulin Sensitivity Independently of Body Weight.

Figure 2:
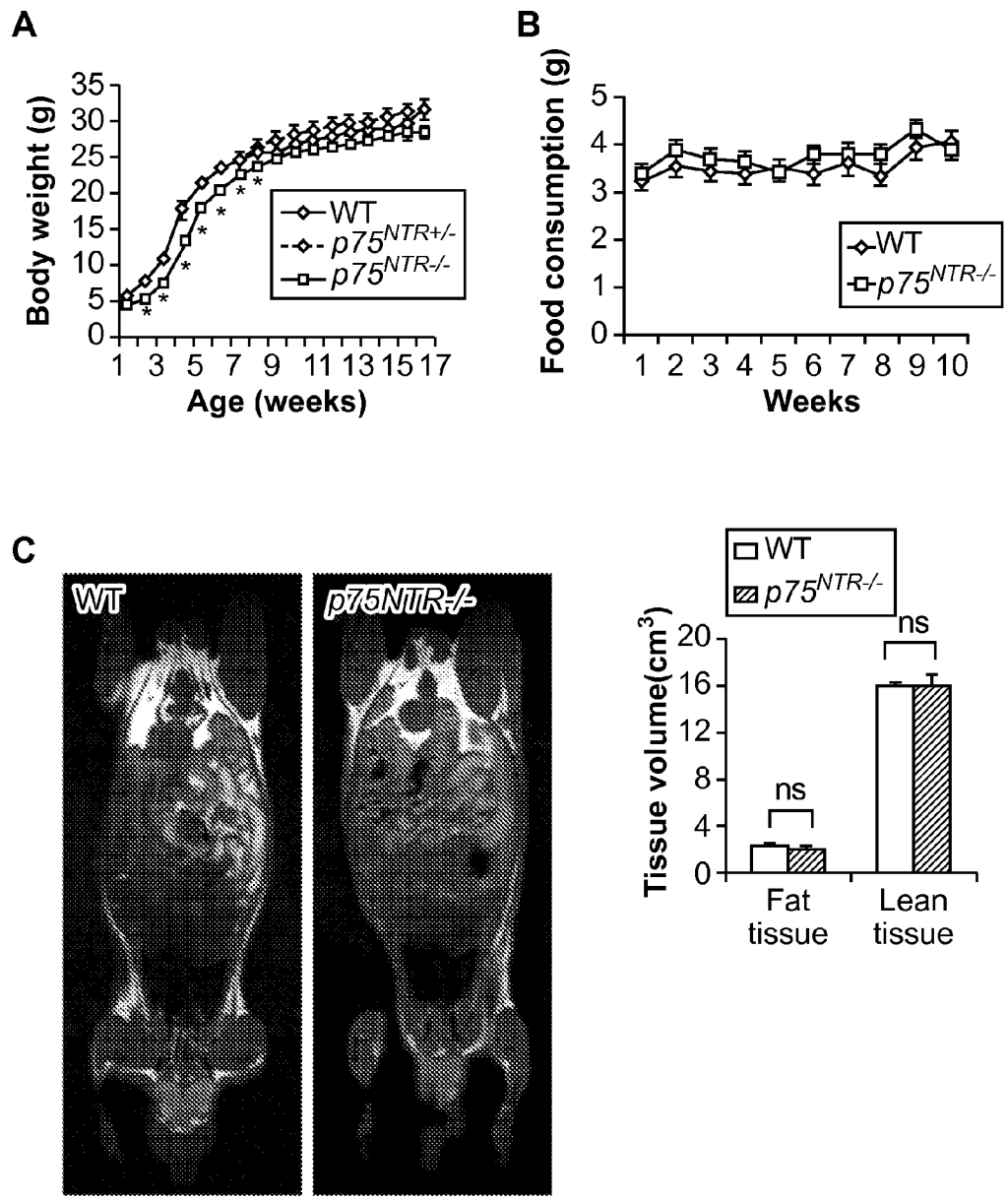
FIGS. 2A-C depict metabolic analysis of $p75^{NTR-/-}$ mice on normal chow.
Figure 3:
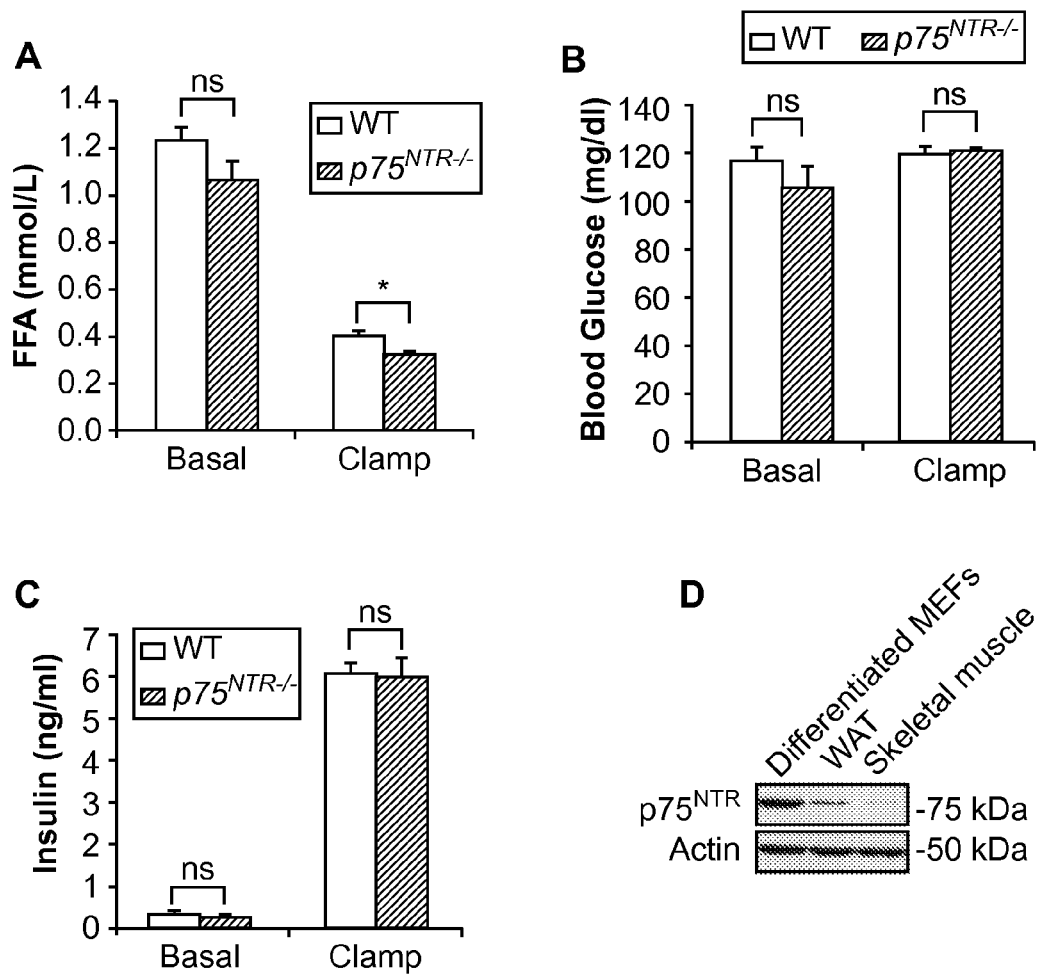
FIGS. 3A-D depict basal levels of free fatty acids (FFA) (A), blood glucose (B), and insulin (C) after claim experiments in wild-type (WT) and $p75^{NTR-/-}$ mice.

On normal chow, $p75^{NTR-/-}$ mice weigh the same as wild-type (WT) mice (FIG. 1A and FIG. 2A), consume the same amount of food (FIG. 2B), and show similar body composition (FIG. 26), suggesting that loss of $p75^{NTR}$ does not regulate appetite or body weight on normal diet. To determine if $p75^{NTR}$ regulates other metabolic pathways, glucose and insulin homeostasis were tested in WT and $p75^{NTR-/-}$ mice. $p75^{NTR-/-}$ mice showed lowered glycemic excursions during glucose tolerance tests (GTTs) (50% decrease in AUC) (FIG. 1B) with a 30% increase in the hypoglycemic effect of insulin during insulin tolerance tests (ITT) (FIGS. 1C and D) compared to WT controls. These findings indicate that lean, chow-fed $p75^{NTR-/-}$ mice are insulin sensitive relative to weight-matched lean controls, and this was quantitated by euglycemic-hyperinsulinemic glucose clamp studies. As seen in FIG. 1E, the glucose disposal rate (GDR) was greater in $p75^{NTR-/-}$ mice, as was the insulin stimulated GDR (IS-GDR) value (FIG. 1F) compared to WT mice. Basal hepatic glucose production (HGP) was not affected by $p75^{NTR}$ deficiency, but suppression of HGP by insulin was significantly improved (FIG. 1G) by 20% (FIG. 1H). Furthermore, free fatty acid (FFA) levels were lower in the $p75^{NTR-/-}$ mice during the clamp studies, while basal FFA, glucose and insulin levels were unchanged (FIG. 3A-C). It is important to note that genetic manipulations that improve insulin sensitivity in lean, normal chow-fed mice are unusual, and these results demonstrate significantly enhanced insulin sensitivity in $p75^{NTR-/-}$ mice independent of food intake or body weight.

FIG. 1.

$p75^{NTR-/-}$ mice exhibit improved insulin sensitivity on normal diet. (A) Body weight of WT and $p75^{NTR-/-}$ mice on normal chow (n=10; ns, not significant). (B) Glucose tolerance of fasted WT and $p75^{NTR-/-}$ mice on normal chow (n=10, *P<0.05, P<0.01, *P<0.001). (C) Insulin tolerance of fasted WT and $p75^{NTR-/-}$ mice on normal chow (n=10, P<0.01, *P<0.001). (D) Percentage of initial blood glucose in insulin tolerance test (n=10, *P<0.05). (E) Glucose disposal rates (GDR) from WT and $p75^{NTR-/-}$ mice on normal chow (n=10, **P<0.01). (F) Insulin-stimulated glucose disposal rates (IS-GDR) of WT and $p75^{NTR-/-}$ mice on normal chow (n=10, *P<0.05). (G) Hepatic glucose production (HGP) from WT and $p75^{NTR-/-}$ mice on normal chow (n=10, *P<0.05). (H) Suppression of HGP in WT and $p75^{NTR-/-}$ mice on normal chow (n=10, *P<0.05). Data are shown as the means±SEM. Statistical comparisons between means were made with one-way ANOVA (B, C and D) and Student's t test (E, F, G and H).

FIG. 2.

Metabolic analysis of $p75^{NTR-/-}$ mice on normal chow. (A) Body weight on normal chow of $p75^{NTR+/+}$ (n=4), $p75^{NTR+/-}$ (n=5) and $p75^{NTR-/-}$ (n=7) mice. (*P<0.05). Data are shown as the means±SEM. Statistical comparisons between means were made with one-way ANOVA. (B) Food consumption on normal chow of WT and $p75^{NTR-/-}$ mice (n=5). (C) MRI images from 10 week old WT (n=4) and $p75^{NTR-/-}$ mice (n=5) on normal chow (left). Fat and lean tissue volumes (cm³) from the WT and $p75^{NTR-/-}$ mice analyzed by MRI (ns, not significant by Student's t test) (right).

FIG. 3.

(A) Basal levels of FFA after clamp experiments in WT and $p75^{NTR-/-}$ mice (n=10) (ns, not significant; *P<0.05). (B) Basal levels of blood glucose after clamp experiments in WT and $p75^{NTR-/-}$ mice (n=10) (ns, not significant). (C) Basal levels of insulin after clamp experiments in WT and $p75^{NTR-/-}$ mice (n=10) (ns, not significant). "Basal" refers to the values for each of these measures after an overnight fast. "Clamp" refers to the values for each of these measures after the clamp period. (D) Western blot analysis for $p75^{NTR}$ in MEF-derived adipocytes, WAT and skeletal muscle. Representative blot from three independent experiments is shown. Data are shown as the means±SEM. Statistical comparisons between means were made with one-way ANOVA.

Loss of $p75^{NTR}$ Increases Glucose Uptake.

Figure 4:
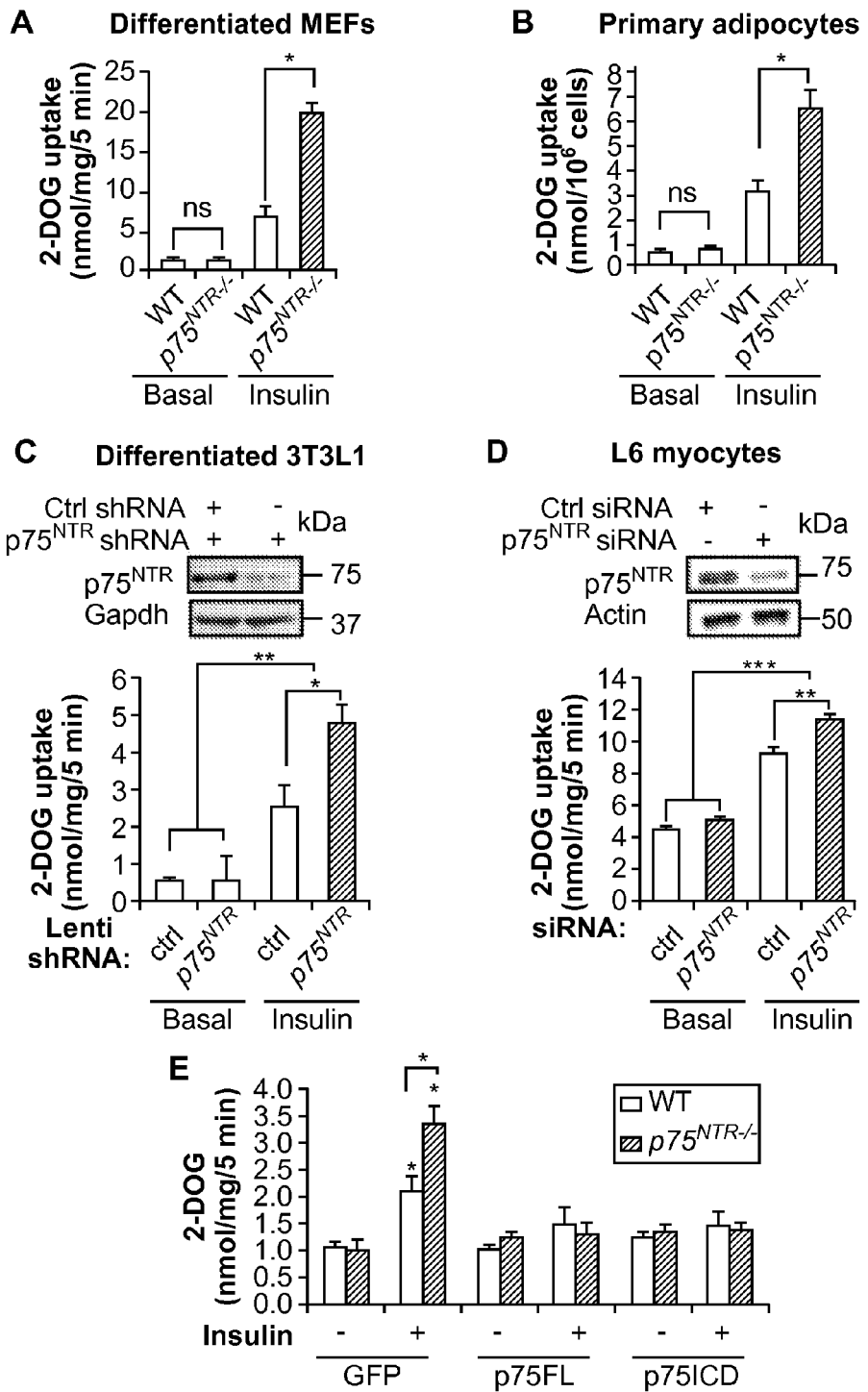
FIGS. 4A-E depict regulation of glucose uptake by $p75^{NTR}$ in adipocytes and skeletal muscle cells.

The mechanisms by which $p75^{NTR}$ might regulate insulin sensitivity in cell autonomous in vitro systems were explored. Since $p75^{NTR-/-}$ mice displayed increased in vivo glucose disposal (FIG. 1E), the effects of $p75^{NTR}$ on insulin-stimulated glucose uptake was examined in adipocytes and myocytes. Adipocytes derived from $p75^{NTR-/-}$ mouse embryonic fibroblasts (MEFs) showed a 3-fold increase in insulin-stimulated glucose uptake compared to WT (FIG. 4A), while basal glucose uptake was identical between WT and $p75^{NTR-/-}$ MEF-derived adipocytes (FIG. 4A). Similar differences in insulin-stimulated glucose transport were observed in primary adipocytes isolated from WT and $p75^{NTR-/-}$ mice (FIG. 4B). Likewise, shRNA knockdown of $p75^{NTR}$ increased insulin-stimulated glucose uptake in 3T3L1 adipocytes (FIG. 46). To analyze the potential role of $p75^{NTR}$ in skeletal muscle, the influence of $p75^{NTR}$ on insulin-stimulated glucose uptake was examined in L6 myocytes. Similar to adipocytes (FIG. 4C), L6 cells transfected with $p75^{NTR}$ siRNA showed no change in basal glucose transport but displayed a significant 20% increase in insulin-stimulated glucose uptake compared to cells transfected with a control siRNA (FIG. 4D). Efficiency of the $p75^{NTR}$ knockdown in 3T3L1 adipocytes and L6 myoblasts (FIG. 4C, D), and expression of $p75^{NTR}$ in MEF-derived adipocytes, WAT and skeletal muscle (FIG. 3D) is shown by immunoblot.

Consistent with the results of $p75^{NTR}$ depletion, overexpression of full-length $p75^{NTR}$ (p75FL) rescued the increase in glucose uptake in $75^{NTR-/-}$ adipocytes (FIG. 4E). The intracellular domain (ICD) of $p75^{NTR}$, which lacks the extracellular domain that binds neurotrophins, was also overexpressed. Similar to the p75FL, the p75ICD also rescued the increase in glucose uptake in $p75^{NTR-/-}$ adipocytes (FIG. 4E), while p75FL and p75ICD decreased glucose uptake in WT adipocytes (FIG. 4E, 5A). These results indicate that the ability of $p75^{NTR}$ to regulate glucose uptake is neurotrophin independent. Consistent with this, addition of the $p75^{NTR}$ neurotrophin ligands Nerve Growth Factor (NGF) or Brain Derived Neurotrophin Factor (BDNF) did not affect glucose uptake (FIG. 5B). Together, these results indicate that $p75^{NTR}$ regulates glucose uptake in adipocytes and myoblasts, and are consistent with the improved in vivo insulin sensitivity and glucose disposal in $p75^{NTR-/-}$ mice (FIG. 1).

FIG. 4.

$p75^{NTR}$ regulates glucose uptake in adipocytes and skeletal muscle cells. (A) Basal and insulin-stimulated glucose uptake in WT and $p75^{NTR-/-}$ MEF-derived adipocytes (ns, not significant; *P<0.05). (B) Basal and insulin-stimulated glucose uptake in WT and $p75^{NTR-/-}$ primary isolated adipocytes (ns, not significant; *P<0.05). (C) $p75^{NTR}$ expression in 3T3L1 adipocytes infected with $p75^{NTR}$ shRNA or scrambled shRNA lentivirus. Gapdh was used as a loading control (top). Basal and insulin-stimulated glucose uptake in 3T3L1 cells differentiated to adipocytes and infected with lentivirus containing $p75^{NTR}$ shRNA or scrambled shRNA control (*P<0.05; P<0.01) (bottom). (D) $p75^{NTR}$ expression in L6 myocytes tranfected with $p75^{NTR}$ siRNA or siRNA control. Gapdh was used as a loading control (top). Basal and insulin-stimulated glucose uptake in L6 myocytes cells transfected with $p75^{NTR}$ siRNA or siRNA control (P<0.01; ***P<0.001) (bottom). (E) Basal and insulin-stimulated glucose uptake in WT and $p75^{NTR-/-}$ MEF-derived adipocytes electroporated with p75FL, p75ICD or GFP control expression vectors. After 72 h, cells were serum starved for 3 h and then stimulated with 100 nM insulin (*P<0.05). Data are shown as the means±SEM of a minimum of three different experiments performed in triplicate. Statistical comparisons between means were made with one-way ANOVA (A, B and E) and Student's t test (C and D).

Figure 5:
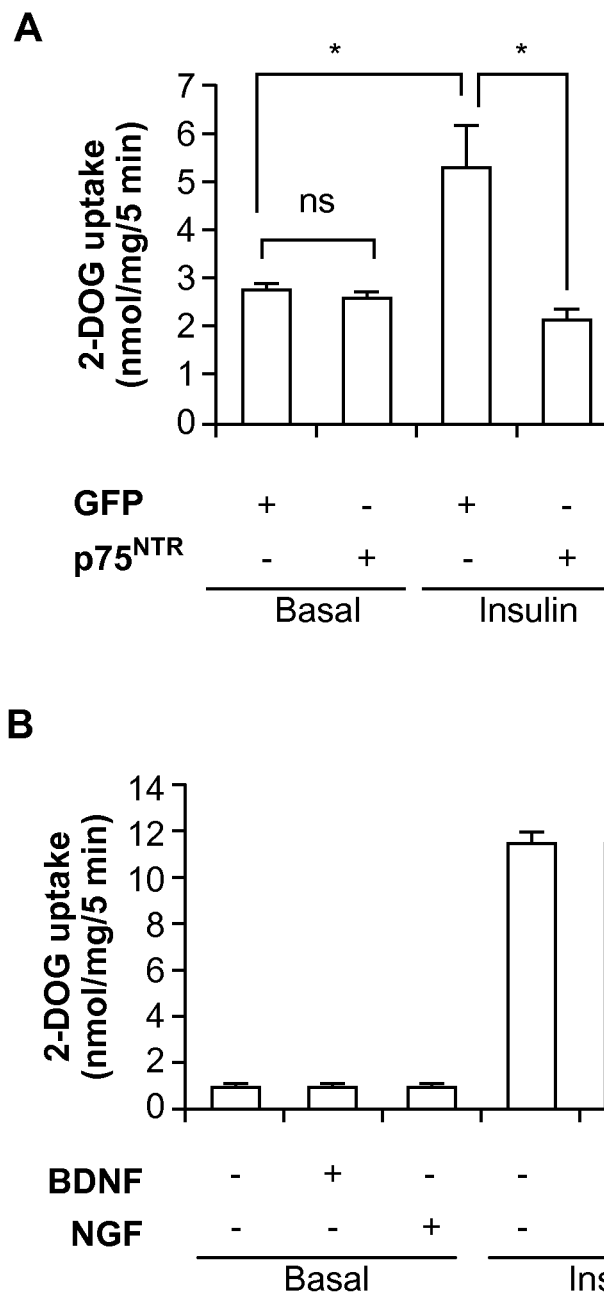
FIGS. 5A and 5B depict basal and insulin-stimulated glucose uptake in 3T3L1 adipocytes.

FIG. 5. (A) Basal and insulin-stimulated glucose uptake in 3T3L1 adipocytes electroporated with $p75^{NTR}$ FL expression vector or GFP control vector. After 72 h, cells were serum starved for 3 h and then stimulated with or without insulin (ns, not significant; *P<0.05). (B) Basal and insulin-stimulated glucose uptake in 3T3L1 adipocytes treated with neurotrophins. No statistically significant differences were observed between basal and insulin-stimulated glucose uptake in 3T3L1 adipocytes treated with NGF or BDNF for 1 h before insulin stimulation. Similar results were obtained after 12 h neurotrophin treatment (not shown). Data are shown as the means±SEM of a minimum of three different experiments performed in triplicate. Statistical comparisons between means were made with one-way ANOVA.

$p75^{NTR}$ Regulates GLUT4 Retention.

Figure 6:
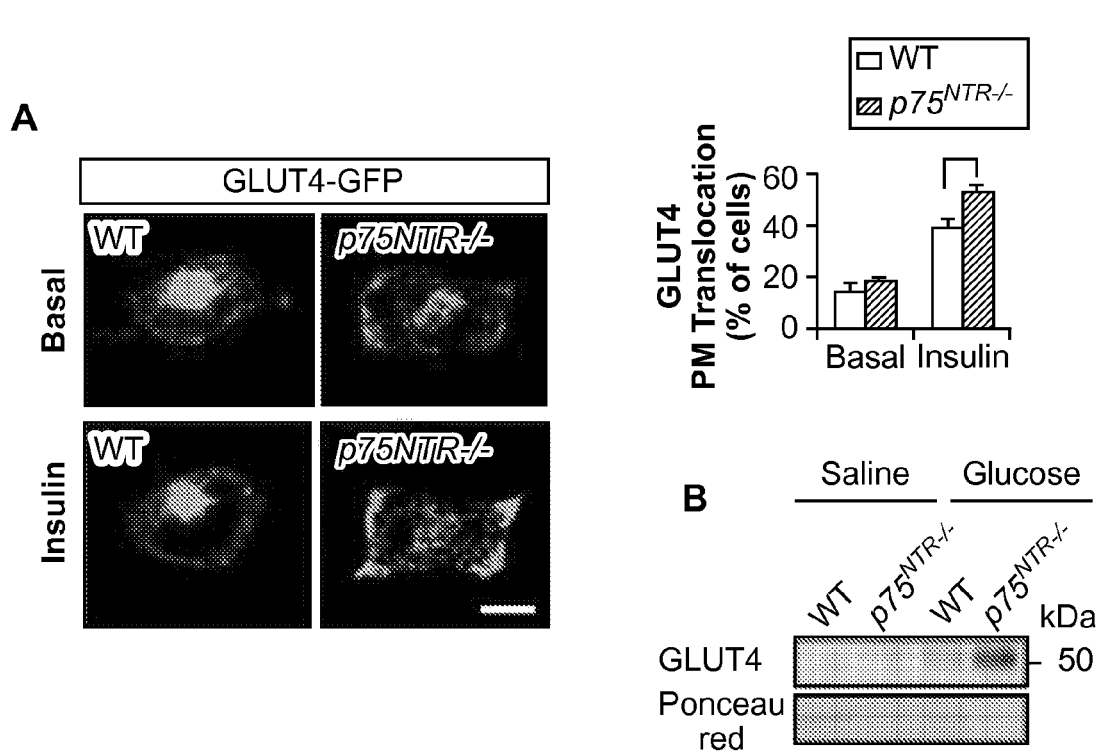
FIGS. 6A and 6B depict regulation of GLUT4 trafficking in adipocytes by $p75^{NTR}$.
Figure 7:
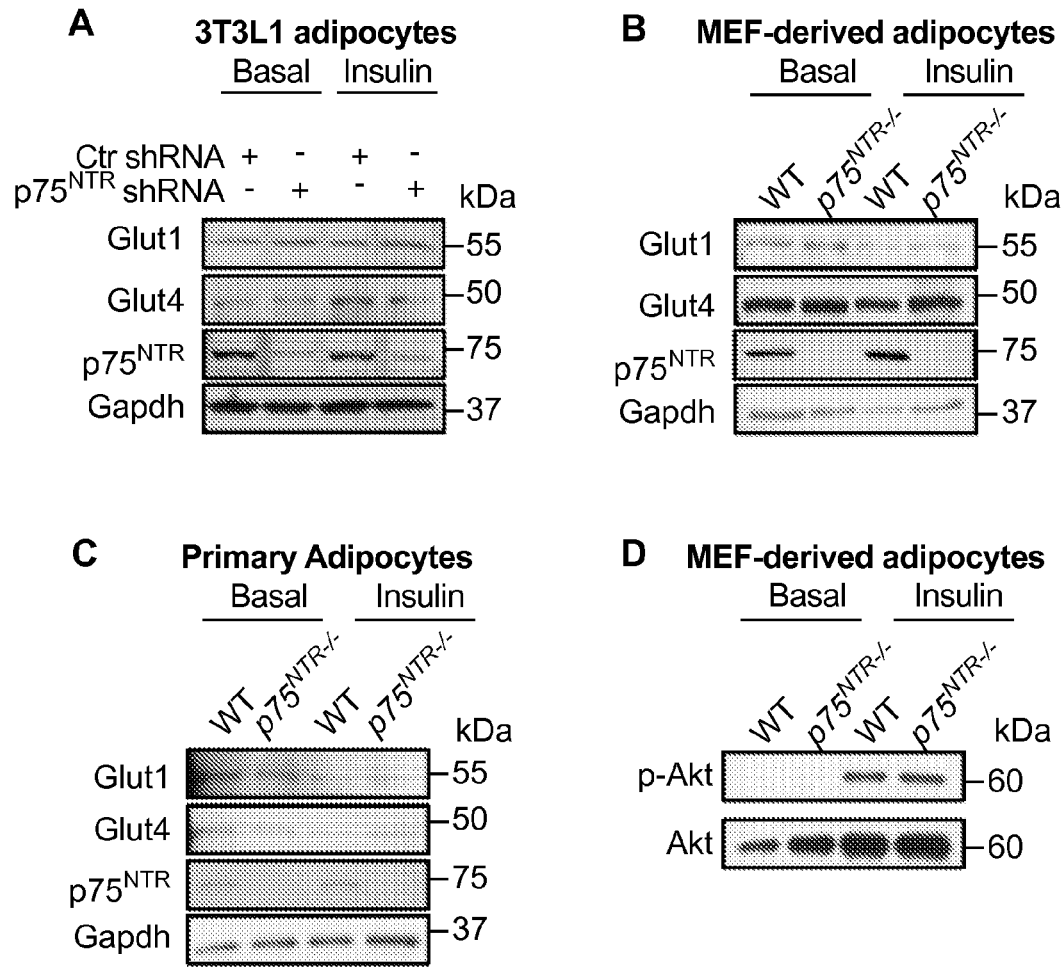
FIGS. 7A-D depict western blots for Glut1, Glut4, and $p75^{NTR}$ in adipocytes.

Since regulation of insulin-stimulated glucose transport is a novel cellular function for $p75^{NTR}$, studies were undertaken to determine the molecular mechanism downstream of $p75^{NTR}$ that regulates glucose uptake. Insulin-stimulated glucose uptake is largely due to translocation of GLUT4 from its basal intracellular location to the plasma membrane (4, 24). To determine if $p75^{NTR}$ regulates GLUT4 trafficking, the intracellular localization of GLUT4-GFP was examined in $p75^{NTR-/-}$ adipocytes. In response to insulin, $p75^{NTR-/-}$ adipocytes exhibited increased GLUT4 translocation to the plasma membrane compared to WT adipocytes (FIG. 6A). Plasma membrane fractionation was also performed from WAT derived from WT and $p75^{NTR-/-}$ mice injected with either saline or glucose to assess translocation of GLUT4 in response to endogenous insulin. As shown in FIG. 6B, plasma membrane GLUT4 content was increased in $p75^{NTR-/-}$ WAT. $p75^{NTR}$ deletion did not affect total protein levels of GLUT1 or GLUT4 in 3T3L1 adipocytes, MEF-derived adipocytes, or primary adipocytes (FIG. 7A-C). Protein levels of $p75^{NTR}$ were shown by immunoblot (FIG. 7A-C). $p75^{NTR}$ also did not affect insulin receptor signaling, as loss of $p75^{NTR}$ did not increase insulin-stimulated Akt phosphorylation (FIG. 7D).

FIG. 6.

$p75^{NTR}$ regulates GLUT4 trafficking in adipocytes. (A) Immunocytochemistry of WT and $p75^{NTR-/-}$ MEF-derived adipocytes transfected with GFP-tagged GLUT4 and stimulated with 100 nM of insulin for 30 min. Scale bar, 75 µm. Representative images of two independent experiments are shown (left). GLUT4 plasma membrane (PM) translocation was quantified by determining the percentage of cells with GFP rim staining. At least 50 cells per condition were counted (*P<0.05 by Student's t test). (B) Western blot for GLUT4 in the plasma membrane fraction of epididymal WAT from WT and $p75^{NTR-/-}$ mice on normal chow injected with (1 g/Kg) of dextrose after 6 h fasting. Ponceau red was used as a loading control.

FIG. 7.

(A) Western blot for Glut1, Glut4 and $p75^{NTR}$ in 3T3L1 adipocytes infected with $p75^{NTR}$ shRNA or scrambled shRNA control containing lentivirus. (B) Western blot for Glut1, Glut4 and $p75^{NTR}$ in WT and $p75^{NTR-/-}$ MEF-derived adipocytes. (C) Western blot for Glut1, Glut4 and $p75^{NTR}$ in primary isolated adipocytes. Gapdh was used as loading control. (D) Western blot for phospho-Akt in WT and $p75^{NTR-/-}$ primary adipocytes. Total Akt was used as a loading control. Representative blots of three independent experiments are shown.

$p75^{NTR}$ Regulates Rab5 and Rab31 Activities.

Figure 8:
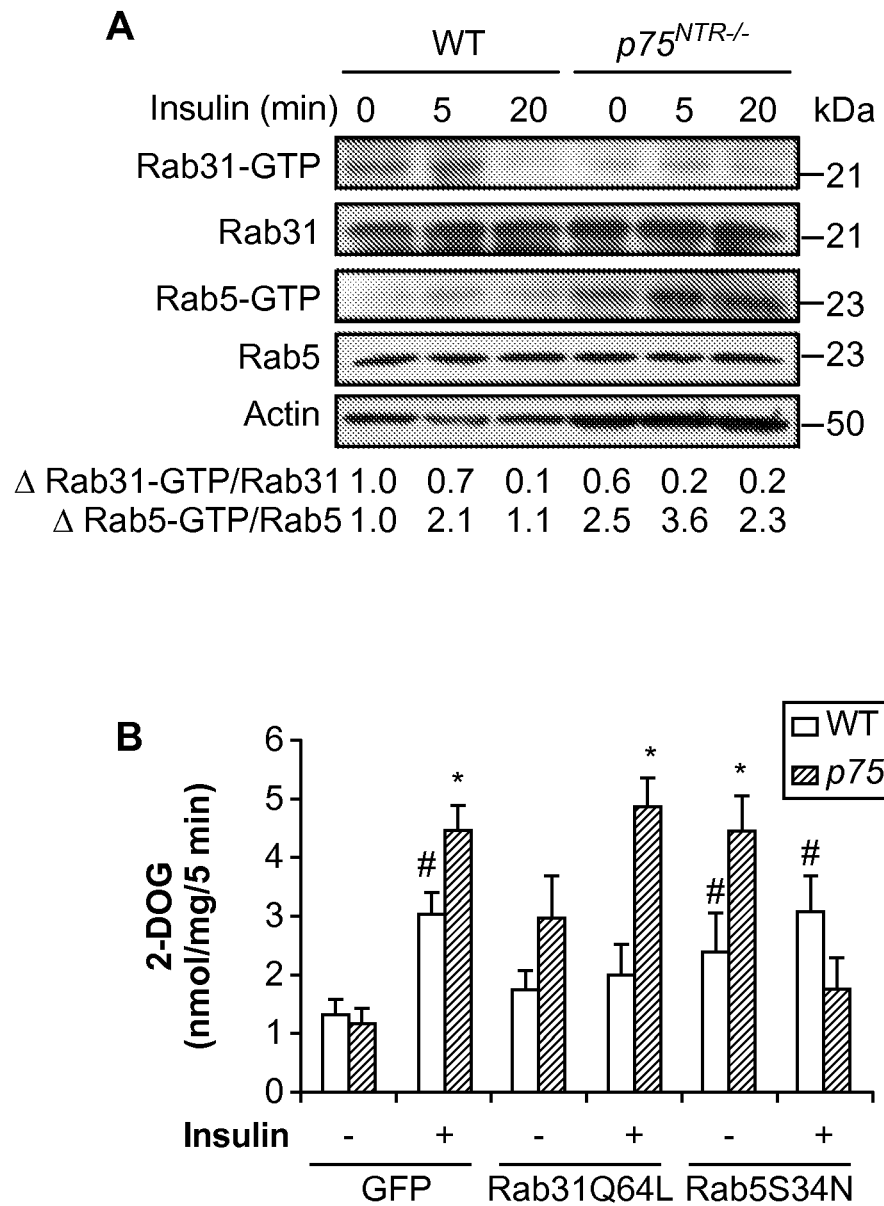
FIGS. 8A and 8B depict regulation of Rab5 and Rab31 GTPase activity by $p75^{NTR}$ in adipocytes.

Stimulation of GLUT4 translocation by insulin results from trafficking of GLUT4 vesicles from intracellular storage sites, and their subsequent fusion with the plasma membrane (4). Activation of Rab5 GTPase functions in the initial endocytosis of GLUT4, thus regulating the intracellular pools of GLUT4 (25). The intracellular retention of GLUT4 is sustained by the activity of Rab31, a Rab5 subfamily GTPase implicated in trans-Golgi network-to-endosome trafficking (6). Insulin decreases the activity of Rab31 in adipocytes, and Rab31 knockdown potentiates insulin-stimulated movement of GLUT4 to the cell surface with increased glucose uptake (6). Since $p75^{NTR}$ is known to regulate other GTPases, such as Rac (23), Ras (21), and RhoA (22), studies were undertaken to determine if $p75^{NTR}$ is required for activation of Rab5 and Rab31. EEA1 binds to Rab5 and Rab31 in a GTP-dependent manner (6). A pull-down assay with EEA1 showed increased activity of Rab5 and decreased activity of Rab31 in p75$^{NTR-/-}$ adipocytes (FIG. 8A), suggesting that loss of p75$^{NTR}$ increases GLUT4 endocytosis, while decreasing GLUT4 intracellular retention. Overexpression of dominant negative Rab5, but not dominant active Rab31, rescued the increased insulin-induced glucose uptake in the p75$^{NTR-/-}$ adipocytes (FIG. 8B). These results suggest that loss of p75$^{NTR}$ differentially regulates Rab5 and Rab31 to increase the flux of GLUT4 through the recycling pathway, while decreasing GLUT4 intracellular retention; thus resulting in increased plasma membrane GLUT4 translocation and glucose uptake.

FIG. 8.

p75$^{NTR}$ regulates Rab5 and Rab31 GTPase activity in adipocytes. (A) WT and p75$^{NTR-/-}$ MEF-derived adipocytes were stimulated with insulin for 5 and 20 min. The activation state of Rab31 and Rab5 was determined using GST-EEA1/NT. Rab31-GTP and Rab5-GTP levels normalized to Rab31 and Rab5, respectively, were quantified by densitometry (Δ represents mean value). Representative blot of three independent experiments is shown. (B) Basal and insulin-stimulated glucose uptake in WT and p75$^{NTR-/-}$ MEF-derived adipocytes electroporated with Rab31Q69L, Rab5S34N or GFP control expression vector. After 72 h, cells were serum starved for 3 h and then stimulated with insulin (*P<0.05 vs WT basal; #P<0.05 vs p75$^{NTR-/-}$ basal). Data are shown as the means±SEM of a minimum of three different experiments performed in triplicate. Statistical comparisons between means were made with one-way ANOVA.

the Rab5 Family GTPases Rab5 and Rab31 Directly Associate with the Death Domain of p75$^{NTR}$.

ICD of p75$^{NTR}$ interacts with several binding partners to regulate cellular functions (26). Co-immunoprecipitation showed interaction of p75$^{NTR}$ with Rab31 (FIG. 9A) and Rab 5 (FIG. 5B). p75$^{NTR}$ also interacted with Gapex5 (FIG. 10A), a Guanine nucleotide Exchange Factor (GEF) for Rab5 and Rab31 (6). Endogenous co-immunoprecipitation showed that p75$^{NTR}$ interacts with Rab31 and Rab5 in 3T3L1 adipocytes (FIG. 9C). p75$^{NTR}$ co-localized with Rab31 and Rab5 in 3T3L1 adipocytes (FIG. 10B). To evaluate the subcellular distribution of p75$^{NTR}$ and Rab5, subcellular fractions of adipocyte were analyzed. The majority of p75$^{NTR}$ protein in adipocytes was localized together with Rab5 in low-density microsomes (LDMs) (FIG. 10C). This is in accordance with prior studies demonstrating that a majority of Rab5 resides in LDM (27). To verify the specificity of the association of p75$^{NTR}$ with Rab5 family GTPases, mapping studies were conducted using deletion mutants (FIG. 9D). Rab5 and Rab31 interact with p75FL, but not p75Δ83, a deletion missing the distal 83 amino acids (FIG. 9E, F), suggesting that the interaction between p75$^{NTR}$ and Rab5 family GTPases occurs within the death domain (DD) of p75$^{NTR}$. As expected, the deletion mutant p75Δ151, which lacks the entire p75ICD, also did not interact with Rab5 and Rab31 (FIG. 9E, F). Overexpression of p75FL suppressed insulin-stimulated glucose uptake, but not p75Δ83 (FIG. 9G), further supporting the involvement of the DD of p75$^{NTR}$ in the regulation of glucose uptake by p75$^{NTR}$.

To further characterize the interaction, peptide array technology, which has defined sites of direct interaction for other p75$^{NTR}$ partners (16, 18) and many other proteins (28), was used. Using Rab5-GST or Rab31-GST, a peptide array library of overlapping 25-mer peptides that spanned the sequence of p75ICD was screened. The strongest interactions were within the DD and in particular within helix 4 and the region between helixes 4 and 5 (peptide 7, aa 386-400) (FIG. 9I). This interaction was distinct from that previously described for binding of RhoGDI within helix 5 of p75ICD (FIG. 10D) (20). In accordance, Tat-Pep5, an inhibitory peptide that blocks the interaction of p75$^{NTR}$ with RhoGDI (20), did not block the interaction of Rab5 with p75ICD (FIG. 9I), further suggesting that different epitopes within the DD of p75$^{NTR}$ contribute to the binding of Rho and the Rab5 family GTPases. These results suggest a direct interaction between p75$^{NTR}$ and the Rab5 family GTPases that primarily requires helix 4 within the death domain of p75$^{NTR}$.

Figure 9:
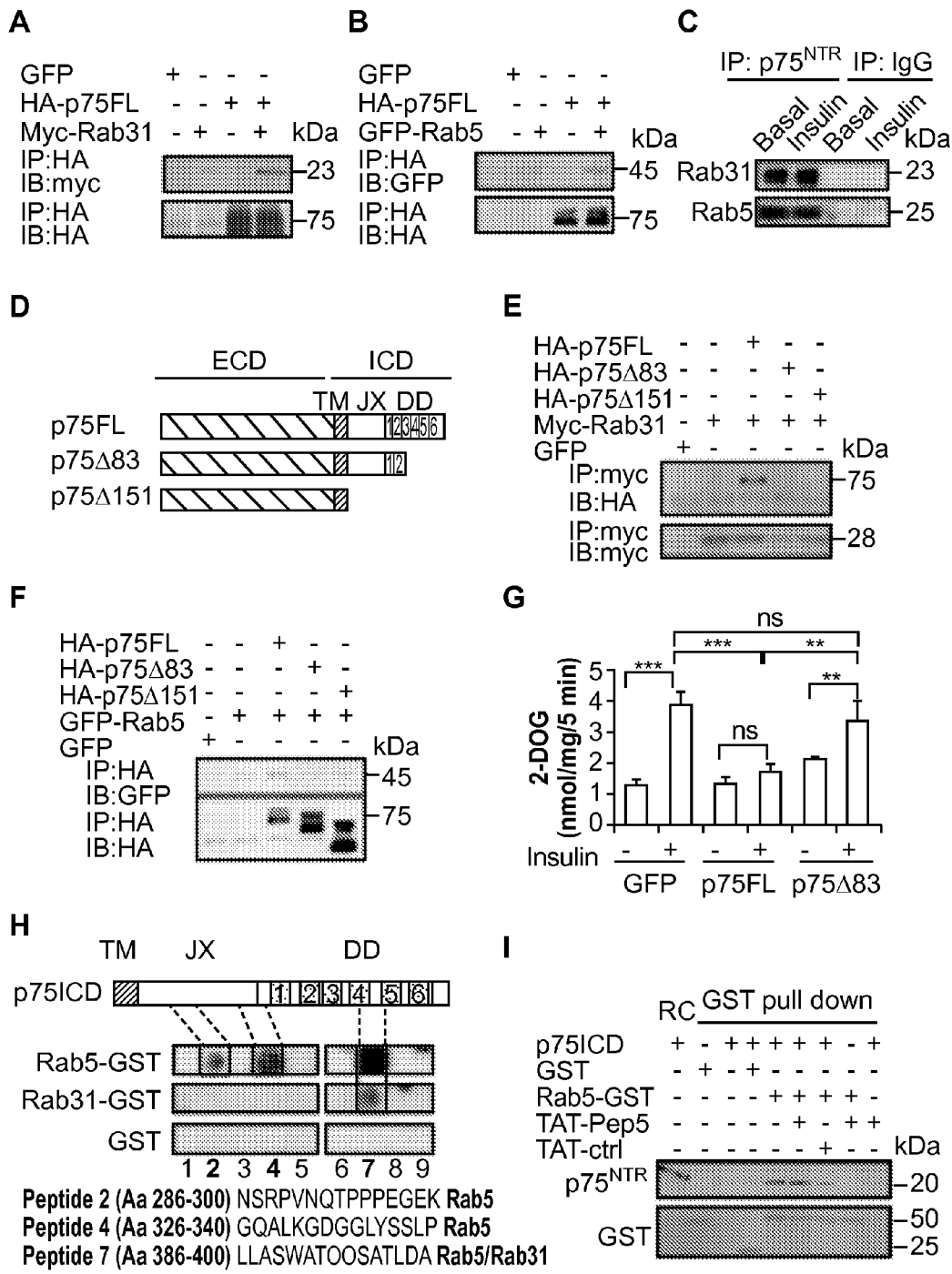
FIGS. 9A-I depict interaction of the death domain of $p75^{NTR}$ with Rab5 and Rab31 GTPases.
Figure 10:
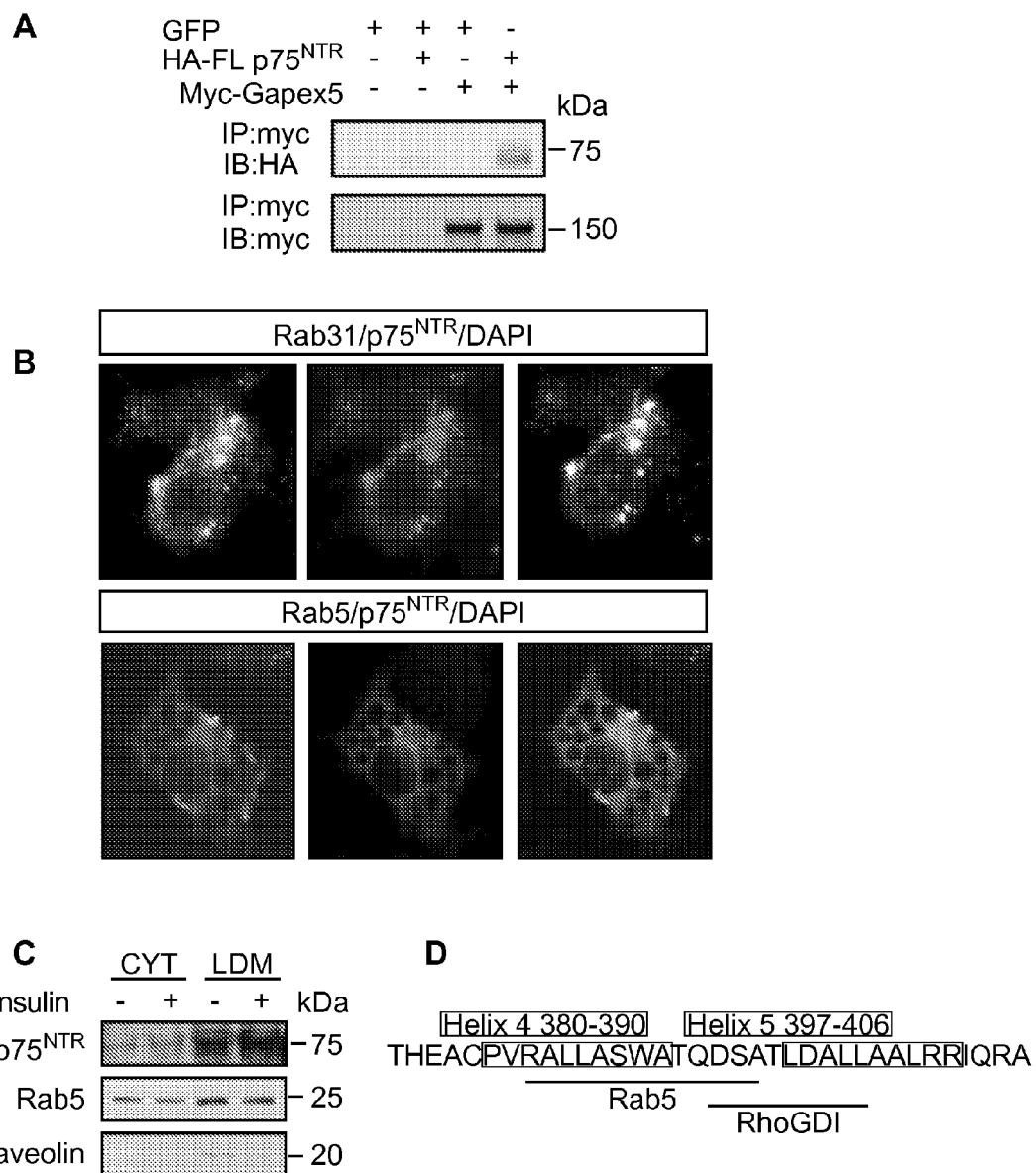
FIG. 10 D depicts the peptide THEACPVRALLASWATQDSATLDALLAALR-RIQRA (SEQ ID NO:35).

FIG. 9. The death domain of p75$^{NTR}$ directly associates with Rab5 and Rab31 GTPases. (A) Immunoprecipitation of HA-FL p75$^{NTR}$ with myc-Rab31 transfected in HEK293T cells. (B) Immunoprecipitation of HA-FL-p75$^{NTR}$ with GFP-Rab5 transfected in HEK293T cells. Lysates were immunoprecipitated with anti-HA antibody, and western blots were developed with anti-GFP and anti-HA antibodies. (C) Immunoprecipitation of p75$^{NTR}$ with Rab31 and Rab5 in 3T3L1 adipocytes stimulated with insulin. Lysates were immunoprecipitated with anti-p75$^{NTR}$ antibody, and western blots were developed with anti-Rab31 and anti-Rab5 antibodies. (D) Schematic diagram of HA-tagged p75FL and deletion mutants Δ83 and Δ151. TM, transmembrane domain; JX, juxtamembrane region; DD, death domain. (E) Mapping of the p75$^{NTR}$ sites required for interaction with Rab31. Immunoprecipitation of myc-Rab31 with truncated forms of HA-p75$^{NTR}$ transfected in HEK293T cells. Lysates were immunoprecipitated with anti-myc antibody, and western blots were developed with anti-HA and anti-myc antibodies. (F) Mapping of the p75$^{NTR}$ sites required for interaction with Rab5. Immunoprecipitation of truncated forms of HA-p75$^{NTR}$ with GFP-Rab5 in HEK293T cells. Lysates were immunoprecipitated with anti-HA antibody, and western blots were developed with anti-GFP and anti-HA antibodies. (G) Basal and insulin-stimulated glucose uptake of WT MEF-derived adipocytes electroporated with p75FL, p75Δ83 or GFP control expression vectors. After 72 h, cells were serum starved for 3 h and then stimulated with 100 nM insulin (P<0.01; *P<0.001; ns, not significant). Data are shown as the means±SEM of two different experiments performed in triplicate. Statistical comparisons between means were made with one-way ANOVA. (H) Peptide array mapping of the p75$^{NTR}$ ICD sites required for the interaction with Rab5 and Rab31. Schematic diagram of the p75$^{NTR}$ ICD shows the domain organization. The six helixes within the DD are highlighted in yellow. Peptide array screened with recombinant GST-Rab5 and GST-Rab31 revealed helix 4 of p75$^{NTR}$ ICD as the strongest region that interacts with Rab5 and Rab31. Peptide location, length, and sequences are shown. Peptide library was also screened with recombinant GST as a control. (I) Co-immunoprecipitation of p75ICD and activated GST-Rab5 recombinant proteins. Tat-Pep5 or Tat control peptide (Tat-ctrl) were added as indicated. GST-Rab5 was immunoprecipitated with anti-GST antibody, and western blots were developed with anti-p75$^{NTR}$ and anti-GST antibodies. Western blots were performed in triplicates and in all panels representative blots are shown.

FIG. 10.

(A) Immunoprecipitation of myc-GAPEX-5 with HA-FL-p75$^{NTR}$ transfected in HEK293T cells. Lysates were immunoprecipitated with anti-myc antibody, and western blots were developed with anti-HA and anti-myc antibodies. (B) Immunolocalization of p75$^{NTR}$ with Rab31 or Rab5 in 3T3L1 adipocytes. Differentiated 3T3L1 were fixed and immunostained for Rab31 and Rab5 with p75$^{NTR}$. Images show co-immunolocalization of Rab31 and Rab5, respectively with p75$^{NTR}$. (C) Cytosolic (CYT) and low-density microsome (LDM) fractions of 3T3L1 adipocytes show presence of p75$^{NTR}$ and Rab5 in LDMs. Caveolin was used as a membrane fraction marker. (D) Schematic representation of the binding of Rab5 family GTPases and RhoGDI to helixes 4 and 5 of the death domain of p75$^{NTR}$ respectively.

Example 2

Identification of Rab31 Peptides that Bind p75$^{NTR}$ ICD

Peptide arrays were manufactured by Kinexus Bioinformatics Corporation (Vancouver, Canada). Synthetic overlapping peptides (25 amino acids in length) for Rab31 were spotted on nitrocellulose membranes. Membranes were overlaid with 1 μg/ml recombinant GST-p75$^{NTR}$ ICD. Bound recombinant GST-p75ICD were detected using rabbit anti-p75$^{NTR}$ (1:1000, Millipore) followed by secondary anti-rabbit horseradish peroxidase antibody (1:5000, Cell Signaling).

Figure 16:
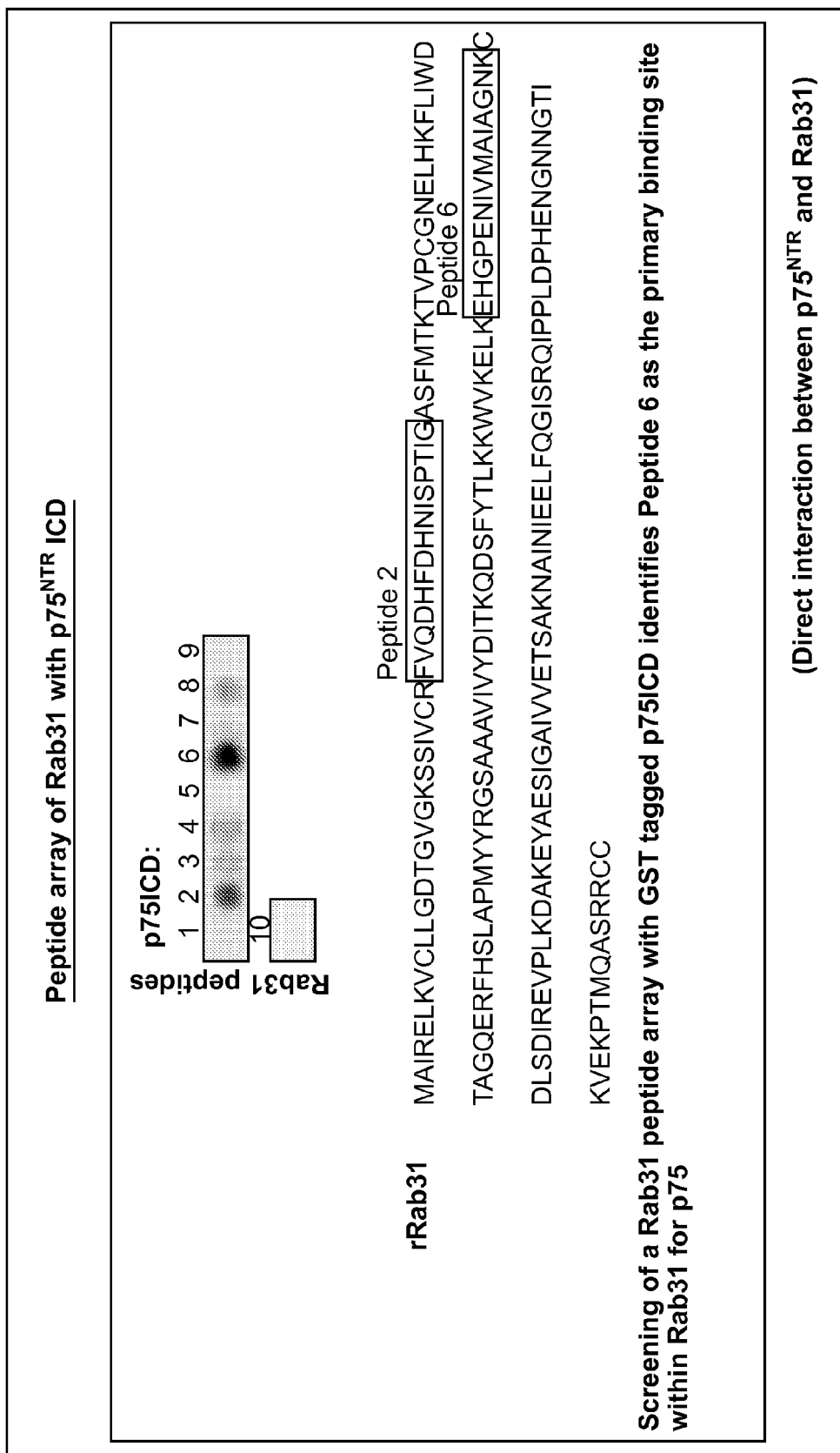
FIG. 16 depicts peptide array data of Rab31 peptides with $p75^{NTR}$ intracellular domain (ICD). Rab31 (SEQ ID NO:54); Rab31 Peptide 2 (SEQ ID NO:55); Rab31 Peptide 6 (SEQ ID NO:17).

As shown in FIG. 16, Peptide 6 was identified as a Rab31 peptide that binds p75$^{NTR}$ ICD.

REFERENCES

1. Herman M A & Kahn B B (2006) Glucose transport and sensing in the maintenance of glucose homeostasis and metabolic harmony. *J Clin Invest* 116:1767-1775.
2. Muoio D M & Newgard C B (2008) Mechanisms of disease: molecular and metabolic mechanisms of insulin resistance and beta-cell failure in type 2 diabetes. *Nat Rev Mol Cell Biol* 9:193-205.
3. Graham T E & Kahn B B (2007) Tissue-specific alterations of glucose transport and molecular mechanisms of intertissue communication in obesity and type 2 diabetes. *Horm Metab Res* 39:717-721.
4. Hou J C & Pessin J E (2007) Ins (endocytosis) and outs (exocytosis) of GLUT4 trafficking. *Curr Opin Cell Biol* 19:466-473.
5. Dugani C B & Klip A (2005) Glucose transporter 4: cycling, compartments and controversies. *EMBO Rep* 6:1137-1142.
6. Lodhi I J, et al. (2007) Gapex-5, a Rab31 guanine nucleotide exchange factor that regulates Glut4 trafficking in adipocytes. *Cell Metab* 5:59-72.
7. Chao M V (2003) Neurotrophins and their receptors: a convergence point for many signalling pathways. *Nat Rev Neurosci* 4:299-309.
8. Lomen-Hoerth C & Shooter E M (1995) Widespread Neurotrophin Receptor Expression in the Immune System and Other Normeuronal Rat Tissues. *J Neurochem* 64:1780-1789.
9. Peeraully M R, Jenkins J R, & Trayhurn P (2004) NGF gene expression and secretion in white adipose tissue: regulation in 3T3-L1 adipocytes by hormones and inflammatory cytokines. *Am J Physiol Endocrinol Metab* 287: E331-339.
10. Deponti D, et al. (2009) The low-affinity receptor for neurotrophins p75NTR plays a key role for satellite cell function in muscle repair acting via RhoA. *Mol Biol Cell* 20:3620-3627.
11. Reddypalli S, et al. (2005) p75NTR-mediated signaling promotes the survival of myoblasts and influences muscle strength. *J Cell Physiol* 204:819-829.
12. Baron P, et al. (1994) Expression of the low-affinity NGF receptor during human muscle development, regeneration, and in tissue culture. *Muscle Nerve* 17:276-284.
13. Teng K K & Hempstead B L (2004) Neurotrophins and their receptors: signaling trios in complex biological systems. *Cell Mol Life Sci* 61:35-48.
14. Reichardt L F (2006) Neurotrophin-regulated signalling pathways. *Philos Trans R Soc Lond B Biol Sci* 361:1545-1564.
15. Passino M A, Adams R A, Sikorski S L, & Akassoglou K (2007) Regulation of hepatic stellate cell differentiation by the neurotrophin receptor p75NTR. *Science* 315:1853-1856.
16. Sachs B D, et al. (2007) p75 neurotrophin receptor regulates tissue fibrosis through inhibition of plasminogen activation via a PDE4/cAMP/PKA pathway. *J Cell Biol* 177:1119-1132.
17. Lee K F, et al. (1992) Targeted mutation of the gene encoding the low affinity NGF receptor p75 leads to deficits in the peripheral sensory nervous system. *Cell* 69:737-749.
18. Le Moan N, Houslay D M, Christian F, Houslay M D, & Akassoglou K (2011) Oxygen-Dependent Cleavage of p75 Neurotrophin Receptor Triggers Stabilization of HIF-1 alpha. *Mol Cell* 44:476-490.
19. Rabizadeh S, et al. (1993) Induction of apoptosis by the low-affinity NGF receptor. *Science* 261:345-348.
20. Yamashita T & Tohyama M (2003) The p75 receptor acts as a displacement factor that releases Rho from Rho-GDI. *Nat Neurosci* 6:461-467.
21. Blochl A, Blumenstein L, & Ahmadian M R (2004) Inactivation and activation of Ras by the neurotrophin receptor p75. *Eur J Neurosci* 20:2321-2335.
22. Yamashita T, Tucker K L, & Barde Y A (1999) Neurotrophin binding to the p75 receptor modulates Rho activity and axonal outgrowth. *Neuron* 24:585-593.
23. Harrington A W, Kim J Y, & Yoon S O (2002) Activation of Rac GTPase by p75 is necessary for c-jun N-terminal kinase-mediated apoptosis. *J Neurosci* 22:156-166.
24. Huang S & Czech M P (2007) The GLUT4 glucose transporter. *Cell Metab* 5:237-252.
25. Huang J, Imamura T, & Olefsky J M (2001) Insulin can regulate GLUT4 internalization by signaling to Rab5 and the motor protein dynein. *Proc Natl Acad Sci USA* 98:13084-13089.
26. Barker P A (2004) p75NTR is positively promiscuous: novel partners and new insights. *Neuron* 42:529-533.
27. Lodhi I J, et al. (2008) Insulin stimulates phosphatidylinositol 3-phosphate production via the activation of Rab5. *Mol Biol Cell* 19:2718-2728.
28. Bolger G B, et al. (2006) Scanning peptide array analyses identify overlapping binding sites for the signalling scaffold proteins, beta-arrestin and RACK1, in cAMP-specific phosphodiesterase PDE4D5. *Biochem J* 398:23-36.
29. Deinhardt K, Reversi A, Berninghausen O, Hopkins C R, & Schiavo G (2007) Neurotrophins Redirect p75NTR from a clathrin-independent to a clathrin-dependent endocytic pathway coupled to axonal transport. *Traffic* 8:1736-1749.
30. Deinhardt K, et al. (2006) Rab5 and Rab7 control endocytic sorting along the axonal retrograde transport pathway. *Neuron* 52:293-305.
31. Kaddai V, Le Marchand-Brustel Y, & Cormont M (2008) Rab proteins in endocytosis and Glut4 trafficking *Acta Physiol (Oxf)* 192:75-88.

32. Machner M P & Isberg R R (2007) A bifunctional bacterial protein links GDI displacement to Rab1 activation. *Science* 318:974-977.
33. Harrington A W, et al. (2008) The role of Kalirin9 in p75/nogo receptor-mediated RhoA activation in cerebellar granule neurons. *J Biol Chem* 283:24690-24697.
34. Liepinsh E, Ilag L L, Otting G, & Ibanez C F (1997) NMR structure of the death domain of the p75 neurotrophin receptor. *Embo J* 16:4999-5005.
35. Xu B, et al. (2003) Brain-derived neurotrophic factor regulates energy balance downstream of melanocortin-4 receptor. *Nat Neurosci* 6:736-742.
36. Yeo G S, et al. (2004) A de novo mutation affecting human TrkB associated with severe obesity and developmental delay. *Nat Neurosci* 7:1187-1189.
37. Lyons W E, et al. (1999) Brain-derived neurotrophic factor-deficient mice develop aggressiveness and hyperphagia in conjunction with brain serotonergic abnormalities. *Proc Natl Acad Sci USA* 96:15239-15244.
38. Yamanaka M, et al. (2007) Brain-derived neurotrophic factor enhances glucose utilization in peripheral tissues of diabetic mice. *Diabetes Obes Metab* 9:59-64.
39. Nakagawa T, et al. (2003) Anti-obesity and anti-diabetic effects of brain-derived neurotrophic factor in rodent models of leptin resistance. *Int J Obes Relat Metab Disord* 27:557-565.
40. Yamanaka M, et al. (2008) Intermittent administration of brain-derived neurotrophic factor (BDNF) ameliorates glucose metabolism and prevents pancreatic exhaustion in diabetic mice. *J Biosci Bioeng* 105:395-402.
41. Hempstead BL (2002) The many faces of p75NTR. *Curr Opin Neurobiol* 12:260-267.
42. Gao Y, Nikulina E, Mellado W, & Filbin M T (2003) Neurotrophins elevate cAMP to reach a threshold required to overcome inhibition by MAG through extracellular signal-regulated kinase-dependent inhibition of phosphodiesterase. *J Neurosci* 23:11770-11777.
43. Wang K C, Kim J A, Sivasankaran R, Segal R, & He Z (2002) P75 interacts with the Nogo receptor as a co-receptor for Nogo, MAG and OMgp. *Nature* 420:74-78.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reducing blood glucose levels and/or insulin resistance in an individual, the method comprising administering to the individual an effective amount of an agent that inhibits binding between the intracellular domain of the p75 neurotrophin receptor (p75$^{NTR}$) and an intracellular GTPase selected from Rab31 and Rab5, wherein the agent is a peptide comprising an amino acid sequence selected from:

| | | |
|---|---|---|
| a) | LLASWATQDSATLDA; | (SEQ ID NO: 1) |
| b) | X$_1$LASWATQDSATLDA; | (SEQ ID NO: 2) |
| c) | LX$_1$ASWATQDSATLDA; | (SEQ ID NO: 3) |
| d) | LLX$_1$SWATQDSATLDA; | (SEQ ID NO: 4) |
| e) | LLAX$_1$WATQDSATLDA; | (SEQ ID NO: 5) |
| f) | LLASX$_1$ATQDSATLDA; | (SEQ ID NO: 6) |
| g) | LLASWX$_1$TQDSATLDA; | (SEQ ID NO: 7) |
| h) | LLASWAX$_1$QDSATLDA; | (SEQ ID NO: 8) |
| i) | LLASWATX$_1$DSATLDA; | (SEQ ID NO: 9) |
| j) | LLASWATQX$_1$SATLDA; | (SEQ ID NO: 10) |
| k) | LLASWATQDX$_1$ATLDA; | (SEQ ID NO: 11) |
| l) | LLASWATQDSX$_1$TLDA; | (SEQ ID NO: 12) |
| m) | LLASWATQDSAX$_1$LDA; | (SEQ ID NO: 13) |
| n) | LLASWATQDSATX$_1$DA; | (SEQ ID NO: 14) |
| o) and | LLASWATQDSATLX$_1$A; | (SEQ ID NO: 15) |
| p) | LLASWATQDSATLDX$_1$, | (SEQ ID NO: 16) | where X$_1$ is any amino acid.

2. The method of claim 1, wherein the peptide comprises at least one non-coded amino acid.

3. The method of claim 1, wherein the peptide comprises at least one D-amino acid.

4. The method of claim 1, wherein the peptide comprises a non-peptide isosteric linkage.

5. The method of claim 1, wherein the peptide has a length of from 15 amino acids to about 50 amino acids.

6. The method of claim 1, wherein the peptide is cyclized.

7. The method of claim 1, wherein the peptide comprises a protein transduction domain (PTD).

8. The method of claim 1, wherein the agent is a peptide comprising the amino acid sequence LLASWATQDSATLDA (SEQ ID NO:1).

* * * * *

```
                        SEQUENCE LISTING

<160> NUMBER OF SEQ ID NOS: 56

<210> SEQ ID NO 1
<211> LENGTH: 15
<212> TYPE: PRT
<213> ORGANISM: Artificial sequence
<220> FEATURE:
<223> OTHER INFORMATION: Synthetic Peptide

<400> SEQUENCE: 1

Leu Leu Ala Ser Trp Ala Thr Gln Asp Ser Ala Thr Leu Asp Ala
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is any amino acid

<400> SEQUENCE: 2

Xaa Leu Ala Ser Trp Ala Thr Gln Asp Ser Ala Thr Leu Asp Ala
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is any amino acid

<400> SEQUENCE: 3

Leu Xaa Ala Ser Trp Ala Thr Gln Asp Ser Ala Thr Leu Asp Ala
```

```
1               5                  10                  15
```

<210> SEQ ID NO 4
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is any amino acid

<400> SEQUENCE: 4

```
Leu Leu Xaa Ser Trp Ala Thr Gln Asp Ser Ala Thr Leu Asp Ala
1               5                  10                  15
```

<210> SEQ ID NO 5
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is any amino acid

<400> SEQUENCE: 5

```
Leu Leu Ala Xaa Trp Ala Thr Gln Asp Ser Ala Thr Leu Asp Ala
1               5                  10                  15
```

<210> SEQ ID NO 6
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa is any amino acid

<400> SEQUENCE: 6

```
Leu Leu Ala Ser Xaa Ala Thr Gln Asp Ser Ala Thr Leu Asp Ala
1               5                  10                  15
```

<210> SEQ ID NO 7
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa is any amino acid

<400> SEQUENCE: 7

```
Leu Leu Ala Ser Trp Xaa Thr Gln Asp Ser Ala Thr Leu Asp Ala
1               5                  10                  15
```

<210> SEQ ID NO 8
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature

```
<222> LOCATION: (7)..(7)
<223> OTHER INFORMATION: Xaa is any amino acid

<400> SEQUENCE: 8

Leu Leu Ala Ser Trp Ala Xaa Gln Asp Ser Ala Thr Leu Asp Ala
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (8)..(8)
<223> OTHER INFORMATION: Xaa is any amino acid

<400> SEQUENCE: 9

Leu Leu Ala Ser Trp Ala Thr Xaa Asp Ser Ala Thr Leu Asp Ala
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (9)..(9)
<223> OTHER INFORMATION: Xaa is any amino acid

<400> SEQUENCE: 10

Leu Leu Ala Ser Trp Ala Thr Gln Xaa Ser Ala Thr Leu Asp Ala
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (10)..(10)
<223> OTHER INFORMATION: Xaa is any amino acid

<400> SEQUENCE: 11

Leu Leu Ala Ser Trp Ala Thr Gln Asp Xaa Ala Thr Leu Asp Ala
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (11)..(11)
<223> OTHER INFORMATION: Xaa is any amino acid

<400> SEQUENCE: 12

Leu Leu Ala Ser Trp Ala Thr Gln Asp Ser Xaa Thr Leu Asp Ala
1               5                   10                  15

<210> SEQ ID NO 13
<211> LENGTH: 15
```

```
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (12)..(12)
<223> OTHER INFORMATION: Xaa is any amino acid

<400> SEQUENCE: 13

Leu Leu Ala Ser Trp Ala Thr Gln Asp Ser Ala Xaa Leu Asp Ala
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (13)..(13)
<223> OTHER INFORMATION: Xaa is any amino acid

<400> SEQUENCE: 14

Leu Leu Ala Ser Trp Ala Thr Gln Asp Ser Ala Thr Xaa Asp Ala
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (14)..(14)
<223> OTHER INFORMATION: Xaa is any amino acid

<400> SEQUENCE: 15

Leu Leu Ala Ser Trp Ala Thr Gln Asp Ser Ala Thr Leu Xaa Ala
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (15)..(15)
<223> OTHER INFORMATION: Xaa is any amino acid

<400> SEQUENCE: 16

Leu Leu Ala Ser Trp Ala Thr Gln Asp Ser Ala Thr Leu Asp Xaa
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Synthetic Peptide

<400> SEQUENCE: 17

Glu His Gly Pro Glu Asn Ile Val Met Ala Ile Ala Gly Asn Lys
1               5                   10                  15
```

```
<210> SEQ ID NO 18
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is any amino acid

<400> SEQUENCE: 18

Glu Xaa Gly Pro Glu Asn Ile Val Met Ala Ile Ala Gly Asn Lys
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa is any amino acid

<400> SEQUENCE: 19

Glu His Xaa Pro Glu Asn Ile Val Met Ala Ile Ala Gly Asn Lys
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is any amino acid

<400> SEQUENCE: 20

Glu His Gly Xaa Glu Asn Ile Val Met Ala Ile Ala Gly Asn Lys
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa is any amino acid

<400> SEQUENCE: 21

Glu His Gly Pro Xaa Asn Ile Val Met Ala Ile Ala Gly Asn Lys
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa is any amino acid
```

```
<400> SEQUENCE: 22

Glu His Gly Pro Xaa Asn Ile Val Met Ala Ile Ala Gly Asn Lys
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (6)..(6)
<223> OTHER INFORMATION: Xaa is any amino acid

<400> SEQUENCE: 23

Glu His Gly Pro Glu Xaa Ile Val Met Ala Ile Ala Gly Asn Lys
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa is any amino acid

<400> SEQUENCE: 24

Glu His Gly Pro Glu Asn Xaa Val Met Ala Ile Ala Gly Asn Lys
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (8)..(8)
<223> OTHER INFORMATION: Xaa is any amino acid

<400> SEQUENCE: 25

Glu His Gly Pro Glu Asn Ile Xaa Met Ala Ile Ala Gly Asn Lys
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (9)..(9)
<223> OTHER INFORMATION: Xaa is any amino acid

<400> SEQUENCE: 26

Glu His Gly Pro Glu Asn Ile Val Xaa Ala Ile Ala Gly Asn Lys
1               5                   10                  15

<210> SEQ ID NO 27
<211> LENGTH: 15
<212> TYPE: PRT
<213> ORGANISM: Artificial sequence
<220> FEATURE:
```

```
<223> OTHER INFORMATION: Synthetic Peptide
<220> FEATURE:
<221> NAME/KEY: misc_feature
<222> LOCATION: (10)..(10)
<223> OTHER INFORMATION: Xaa is any amino acid

<400> SEQUENCE: 27

Glu His Gly Pro Glu Asn Ile Val Met Xaa Ile Ala Gly Asn Lys
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (11)..(11)
<223> OTHER INFORMATION: Xaa is any amino acid

<400> SEQUENCE: 28

Glu His Gly Pro Glu Asn Ile Val Met Ala Xaa Ala Gly Asn Lys
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (12)..(12)
<223> OTHER INFORMATION: Xaa is any amino acid

<400> SEQUENCE: 29

Glu His Gly Pro Glu Asn Ile Val Met Ala Ile Xaa Gly Asn Lys
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (13)..(13)
<223> OTHER INFORMATION: Xaa is any amino acid

<400> SEQUENCE: 30

Glu His Gly Pro Glu Asn Ile Val Met Ala Ile Ala Xaa Asn Lys
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (14)..(14)
<223> OTHER INFORMATION: Xaa is any amino acid

<400> SEQUENCE: 31

Glu His Gly Pro Glu Asn Ile Val Met Ala Ile Ala Gly Xaa Lys
1               5                   10                  15
```

<210> SEQ ID NO 32
<211> LENGTH: 15
<212> TYPE: PRT
<213> ORGANISM: Artificial sequence
<220> FEATURE:
<223> OTHER INFORMATION: Synthetic Peptide
<220> FEATURE:
<221> NAME/KEY: misc_feature
<222> LOCATION: (15)..(15)
<223> OTHER INFORMATION: Xaa is any amino acid

<400> SEQUENCE: 32

Glu His Gly Pro Glu Asn Ile Val Met Ala Ile Ala Gly Asn Xaa
1               5                   10                  15

<210> SEQ ID NO 33
<211> LENGTH: 14
<212> TYPE: PRT
<213> ORGANISM: Artificial sequence
<220> FEATURE:
<223> OTHER INFORMATION: Synthetic Peptide

<400> SEQUENCE: 33

Asn Ser Arg Pro Val Asn Gln Pro Arg Pro Glu Gly Glu Lys
1               5                   10

<210> SEQ ID NO 34
<211> LENGTH: 15
<212> TYPE: PRT
<213> ORGANISM: Artificial sequence
<220> FEATURE:
<223> OTHER INFORMATION: Synthetic Peptide

<400> SEQUENCE: 34

Gly Gln Ala Leu Lys Gly Asp Gly Gly Leu Tyr Ser Ser Leu Pro
1               5                   10                  15

<210> SEQ ID NO 35
<211> LENGTH: 35
<212> TYPE: PRT
<213> ORGANISM: Artificial sequence
<220> FEATURE:
<223> OTHER INFORMATION: Synthetic Peptide

<400> SEQUENCE: 35

Thr His Glu Ala Cys Pro Val Arg Ala Leu Leu Ala Ser Trp Ala Thr
1               5                   10                  15

Gln Asp Ser Ala Thr Leu Asp Ala Leu Leu Ala Ala Leu Arg Arg Ile
            20                  25                  30

Gln Arg Ala
        35

<210> SEQ ID NO 36
<211> LENGTH: 11
<212> TYPE: PRT
<213> ORGANISM: Artificial sequence
<220> FEATURE:
<223> OTHER INFORMATION: Synthetic Peptide

<400> SEQUENCE: 36

Tyr Gly Arg Lys Lys Arg Arg Gln Arg Arg Arg
1               5                   10

<210> SEQ ID NO 37
<211> LENGTH: 12
<212> TYPE: PRT

```
<213> ORGANISM: Artificial sequence
<220> FEATURE:
<223> OTHER INFORMATION: Synthetic Peptide

<400> SEQUENCE: 37

Arg Arg Gln Arg Arg Thr Ser Lys Leu Met Lys Arg
1               5                   10

<210> SEQ ID NO 38
<211> LENGTH: 27
<212> TYPE: PRT
<213> ORGANISM: Artificial sequence
<220> FEATURE:
<223> OTHER INFORMATION: Synthetic Peptide

<400> SEQUENCE: 38

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 39
<211> LENGTH: 33
<212> TYPE: PRT
<213> ORGANISM: Artificial sequence
<220> FEATURE:
<223> OTHER INFORMATION: Synthetic Peptide

<400> SEQUENCE: 39

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 40
<211> LENGTH: 16
<212> TYPE: PRT
<213> ORGANISM: Artificial sequence
<220> FEATURE:
<223> OTHER INFORMATION: Synthetic Peptide

<400> SEQUENCE: 40

Arg Gln Ile Lys Ile Trp Phe Gln Asn Arg Arg Met Lys Trp Lys Lys
1               5                   10                  15

<210> SEQ ID NO 41
<211> LENGTH: 9
<212> TYPE: PRT
<213> ORGANISM: Artificial sequence
<220> FEATURE:
<223> OTHER INFORMATION: Synthetic Peptide

<400> SEQUENCE: 41

Arg Lys Lys Arg Arg Gln Arg Arg Arg
1               5

<210> SEQ ID NO 42
<211> LENGTH: 11
<212> TYPE: PRT
<213> ORGANISM: Artificial sequence
<220> FEATURE:
<223> OTHER INFORMATION: Synthetic Peptide

<400> SEQUENCE: 42
```

```
Tyr Ala Arg Ala Ala Ala Arg Gln Ala Arg Ala
1               5                   10
```

<210> SEQ ID NO 43
<211> LENGTH: 11
<212> TYPE: PRT
<213> ORGANISM: Artificial sequence
<220> FEATURE:
<223> OTHER INFORMATION: Synthetic Peptide

<400> SEQUENCE: 43

```
Thr His Arg Leu Pro Arg Arg Arg Arg Arg
1               5                   10
```

<210> SEQ ID NO 44
<211> LENGTH: 11
<212> TYPE: PRT
<213> ORGANISM: Artificial sequence
<220> FEATURE:
<223> OTHER INFORMATION: Synthetic Peptide

<400> SEQUENCE: 44

```
Gly Gly Arg Arg Ala Arg Arg Arg Arg Arg
1               5                   10
```

<210> SEQ ID NO 45
<211> LENGTH: 427
<212> TYPE: PRT
<213> ORGANISM: Homo sapiens

<400> SEQUENCE: 45

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220
```

```
Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Glu Gly Glu Lys Leu His Ser Asp
        290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 46
<211> LENGTH: 95
<212> TYPE: PRT
<213> ORGANISM: Artificial sequence
<220> FEATURE:
<223> OTHER INFORMATION: Synthetic Peptide

<400> SEQUENCE: 46

Gly Gly Leu Tyr Ser Ser Leu Pro Pro Ala Lys Arg Glu Glu Val Glu
1               5                   10                  15

Lys Leu Leu Asn Gly Ser Ala Gly Asp Thr Trp Arg His Leu Ala Gly
            20                  25                  30

Glu Leu Gly Tyr Gln Pro Glu His Ile Asp Ser Phe Thr His Glu Ala
        35                  40                  45

Cys Pro Val Arg Ala Leu Leu Ala Ser Trp Ala Thr Gln Asp Ser Ala
    50                  55                  60

Thr Leu Asp Ala Leu Leu Ala Ala Leu Arg Arg Ile Gln Arg Ala Asp
65                  70                  75                  80

Leu Val Glu Ser Leu Cys Ser Glu Ser Thr Ala Thr Ser Pro Val
                85                  90                  95

<210> SEQ ID NO 47
<211> LENGTH: 95
<212> TYPE: PRT
<213> ORGANISM: Artificial sequence
<220> FEATURE:
<223> OTHER INFORMATION: Synthetic Peptide

<400> SEQUENCE: 47

Gly Gly Leu Tyr Ser Ser Leu Pro Pro Ala Lys Arg Glu Glu Val Glu
1               5                   10                  15
```

```
Lys Leu Leu Asn Gly Ser Ala Gly Asp Thr Trp Arg His Leu Ala Gly
             20                  25                  30

Glu Leu Gly Tyr Gln Pro Glu His Ile Asp Ser Phe Thr His Glu Ala
         35                  40                  45

Cys Pro Val Arg Ala Leu Leu Ala Ser Trp Ala Thr Gln Asp Ser Ala
 50                  55                  60

Thr Leu Asp Ala Leu Leu Ala Ala Leu Arg Arg Ile Gln Arg Ala Asp
 65                  70                  75                  80

Leu Val Glu Ser Leu Cys Ser Glu Ser Thr Ala Thr Ser Pro Val
                 85                  90                  95

<210> SEQ ID NO 48
<211> LENGTH: 95
<212> TYPE: PRT
<213> ORGANISM: Artificial sequence
<220> FEATURE:
<223> OTHER INFORMATION: Synthetic Peptide

<400> SEQUENCE: 48

Gly Gly Leu Tyr Ser Ser Leu Pro Pro Ala Lys Arg Glu Glu Val Glu
 1               5                  10                  15

Lys Leu Leu Asn Gly Ser Ala Gly Asp Thr Trp Arg His Leu Ala Gly
             20                  25                  30

Glu Leu Gly Tyr Gln Pro Glu His Ile Asp Ser Phe Thr His Glu Ala
         35                  40                  45

Cys Pro Ala Arg Ala Leu Leu Ala Ser Trp Ala Ala Gln Asp Ser Ala
 50                  55                  60

Thr Leu Asp Ala Leu Leu Ala Ala Leu Arg Arg Ile Gln Arg Ala Asp
 65                  70                  75                  80

Ile Val Glu Ser Leu Cys Ser Glu Ser Thr Ala Thr Ser Pro Val
                 85                  90                  95

<210> SEQ ID NO 49
<211> LENGTH: 92
<212> TYPE: PRT
<213> ORGANISM: Artificial sequence
<220> FEATURE:
<223> OTHER INFORMATION: Synthetic Peptide

<400> SEQUENCE: 49

Gly Asn Leu Tyr Ser Ser Leu Pro Leu Thr Lys Arg Glu Glu Val Glu
 1               5                  10                  15

Lys Leu Leu Asn Gly Asp Thr Trp Arg His Leu Ala Gly Glu Leu Gly
             20                  25                  30

Tyr Gln Pro Glu His Ile Asp Ser Phe Thr His Glu Ala Cys Pro Val
         35                  40                  45

Arg Ala Leu Leu Ala Ser Trp Gly Ala Gln Asp Ser Ala Thr Leu Asp
 50                  55                  60

Ala Leu Leu Ala Ala Leu Arg Arg Ile Gln Arg Ala Asp Ile Val Glu
 65                  70                  75                  80

Ser Leu Cys Ser Glu Ser Thr Ala Thr Ser Pro Val
                 85                  90

<210> SEQ ID NO 50
<211> LENGTH: 92
<212> TYPE: PRT
<213> ORGANISM: Artificial sequence
<220> FEATURE:
<223> OTHER INFORMATION: Synthetic Peptide
```

<400> SEQUENCE: 50

Gly Asn Leu Tyr Ser Ser Leu Pro Leu Thr Lys Arg Glu Glu Val Glu
1               5                   10                  15

Lys Leu Leu Asn Gly Asp Thr Trp Arg His Leu Ala Gly Glu Leu Gly
            20                  25                  30

Tyr Gln Pro Glu His Ile Asp Ser Phe Thr His Glu Ala Cys Pro Val
        35                  40                  45

Arg Ala Leu Leu Ala Ser Trp Gly Ala Gln Asp Ser Ala Thr Leu Asp
    50                  55                  60

Ala Leu Leu Ala Ala Leu Arg Arg Ile Gln Arg Ala Asp Ile Val Glu
65                  70                  75                  80

Ser Leu Cys Ser Glu Ser Thr Ala Thr Ser Pro Val
                85                  90

<210> SEQ ID NO 51
<211> LENGTH: 216
<212> TYPE: PRT
<213> ORGANISM: Homo sapiens

<400> SEQUENCE: 51

Met Ala Gly Arg Gly Gly Ala Arg Arg Pro Asn Gly Pro Ala Ala Gly
1               5                   10                  15

Asn Lys Ile Cys Gln Phe Lys Leu Val Leu Leu Gly Glu Ser Ala Val
            20                  25                  30

Gly Lys Ser Ser Leu Val Leu Arg Phe Val Lys Gly Gln Phe His Glu
        35                  40                  45

Tyr Gln Glu Ser Thr Ile Gly Ala Ala Phe Leu Thr Gln Thr Val Cys
    50                  55                  60

Leu Asp Asp Thr Thr Val Lys Phe Glu Ile Trp Asp Thr Ala Gly Gln
65                  70                  75                  80

Glu Arg Tyr His Ser Leu Ala Pro Met Tyr Tyr Arg Gly Ala Gln Ala
                85                  90                  95

Ala Ile Val Val Tyr Asp Ile Thr Asn Thr Asp Thr Phe Ala Arg Ala
            100                 105                 110

Lys Asn Trp Val Lys Glu Leu Gln Arg Gln Ala Ser Pro Asn Ile Val
        115                 120                 125

Ile Ala Leu Ala Gly Asn Lys Ala Asp Leu Ala Ser Lys Arg Ala Val
    130                 135                 140

Glu Phe Gln Glu Ala Gln Ala Tyr Ala Asp Asp Asn Ser Leu Leu Phe
145                 150                 155                 160

Met Glu Thr Ser Ala Lys Thr Ala Met Asn Val Asn Glu Ile Phe Met
                165                 170                 175

Ala Ile Ala Lys Lys Leu Pro Lys Asn Glu Pro Gln Asn Ala Thr Gly
            180                 185                 190

Ala Pro Gly Arg Asn Arg Gly Val Asp Leu Gln Glu Asn Asn Pro Ala
        195                 200                 205

Ser Arg Ser Gln Cys Cys Ser Asn
    210                 215

<210> SEQ ID NO 52
<211> LENGTH: 195
<212> TYPE: PRT
<213> ORGANISM: Homo sapiens

<400> SEQUENCE: 52

Met Met Ala Ile Arg Glu Leu Lys Val Cys Leu Leu Gly Asp Thr Gly
1               5                   10                  15

Val Gly Lys Ser Ser Ile Val Cys Arg Phe Val Gln Asp His Phe Asp
            20                  25                  30

His Asn Ile Ser Pro Thr Ile Gly Ala Ser Phe Met Thr Lys Thr Val
        35                  40                  45

Pro Cys Gly Asn Glu Leu His Lys Phe Leu Ile Trp Asp Thr Ala Gly
    50                  55                  60

Gln Glu Arg Phe His Ser Leu Ala Pro Met Tyr Tyr Arg Gly Ser Ala
65              70                  75                  80

Ala Ala Val Ile Val Tyr Asp Ile Thr Lys Gln Asp Ser Phe Tyr Thr
                85                  90                  95

Leu Lys Lys Trp Val Lys Glu Leu Lys Glu His Gly Pro Glu Asn Ile
            100                 105                 110

Val Met Ala Ile Ala Gly Asn Lys Cys Asp Leu Ser Asp Ile Arg Glu
            115                 120                 125

Val Pro Leu Lys Asp Ala Lys Glu Tyr Ala Glu Ser Ile Gly Ala Ile
        130                 135                 140

Val Val Glu Thr Ser Ala Lys Asn Ala Ile Asn Ile Glu Glu Leu Phe
145                 150                 155                 160

Gln Gly Ile Ser Arg Gln Ile Pro Pro Leu Asp Pro His Glu Asn Gly
                165                 170                 175

Asn Asn Gly Thr Ile Lys Val Glu Lys Pro Thr Met Gln Ala Ser Arg
            180                 185                 190

Arg Cys Cys
        195

<210> SEQ ID NO 53
<211> LENGTH: 1284
<212> TYPE: DNA
<213> ORGANISM: Homo sapiens

<400> SEQUENCE: 53
atgggggcag gtgccaccgg ccgcgccatg gacgggccgc gcctgctgct gttgctgctt      60 ctggggtgt cccttggagg tgccaaggag gcatgcccca caggcctgta cacacacagc     120
ggtgagtgct gcaaagcctg caacctgggc gagggtgtgg cccagccttg tggagccaac     180
cagaccgtgt gtgagccctg cctggacagc gtgacgttct ccgacgtggt gagcgcgacc     240
gagccgtgca agccgtgcac cgagtgcgtg gggctccaga gcatgtcggc cgtgcgtg     300 gaggccgacg acgccgtgtg ccgctgcgcc tacggctact accaggatga gacgactggg     360
cgctgcgagg cgtgccgcgt gtgcgaggcg ggctcgggcc tcgtgttctc ctgccaggac     420
aagcagaaca ccgtgtgcga ggagtgcccc gacggcacgt attccgacga ggccaaccac     480
gtggacccgt gcctgccctg caccgtgtgc gaggacaccg agcgccagct ccgcgagtgc     540
acacgctggg ccgacgccga gtgcgaggag atccctggcc gttggattac acggtccaca     600
cccccagagg gctcggacag cacagccccc agcacccagg agcctgaggc acctccagaa     660
caagacctca tagccagcac ggtggcaggt gtggtgacca cagtgatggg cagctcccag     720
cccgtggtga cccgaggcac caccgacaac ctcatccctg tctattgctc catcctggct     780
gctgtggttg tgggccttgt ggcctacata gccttcaaga ggtggaacag ctgcaagcag     840
aacaagcaag gagccaacag ccggccagtg aaccagacgc ccccaccaga gggagaaaaa     900
ctccacagcg acagtggcat ctccgtggac agccagagcc tgcatgacca gcagccccac     960

-continued

```
acgcagacag cctcgggcca ggccctcaag ggtgacggag gcctctacag cagcctgccc   1020
ccagccaagc gggaggaggt ggagaagctt ctcaacggct ctgcggggga cacctggcgg   1080
cacctggcgg gcgagctggg ctaccagccc gagcacatag actcctttac ccatgaggcc   1140
tgccccgttc gcgccctgct tgcaagctgg gccacccagg acagcgccac actggacgcc   1200
ctcctggccg ccctgcgccg catccagcga gccgacctcg tggagagtct gtgcagtgag   1260
tccactgcca catccccggt gtga                                          1284
```

<210> SEQ ID NO 54
<211> LENGTH: 194
<212> TYPE: PRT
<213> ORGANISM: Artificial sequence
<220> FEATURE:
<223> OTHER INFORMATION: Synthetic Peptide

<400> SEQUENCE: 54

```
Met Ala Ile Arg Glu Leu Lys Val Cys Leu Leu Gly Asp Thr Gly Val
1               5                   10                  15

Gly Lys Ser Ser Ile Val Cys Arg Phe Val Gln Asp His Phe Asp His
                20                  25                  30

Asn Ile Ser Pro Thr Ile Gly Ala Ser Phe Met Thr Lys Thr Val Pro
            35                  40                  45

Cys Gly Asn Glu Leu His Lys Phe Leu Ile Trp Asp Thr Ala Gly Gln
    50                  55                  60

Glu Arg Phe His Ser Leu Ala Pro Met Tyr Tyr Arg Gly Ser Ala Ala
65                  70                  75                  80

Ala Val Ile Val Tyr Asp Ile Thr Lys Gln Asp Ser Phe Tyr Thr Leu
                85                  90                  95

Lys Lys Trp Val Lys Glu Leu Lys Glu His Gly Pro Glu Asn Ile Val
            100                 105                 110

Met Ala Ile Ala Gly Asn Lys Cys Asp Leu Ser Asp Ile Arg Glu Val
        115                 120                 125

Pro Leu Lys Asp Ala Lys Glu Tyr Ala Glu Ser Ile Gly Ala Ile Val
    130                 135                 140

Val Glu Thr Ser Ala Lys Asn Ala Ile Asn Ile Glu Glu Leu Phe Gln
145                 150                 155                 160

Gly Ile Ser Arg Gln Ile Pro Pro Leu Asp Pro His Glu Asn Gly Asn
                165                 170                 175

Asn Gly Thr Ile Lys Val Glu Lys Pro Thr Met Gln Ala Ser Arg Arg
            180                 185                 190

Cys Cys
```

<210> SEQ ID NO 55
<211> LENGTH: 15
<212> TYPE: PRT
<213> ORGANISM: Artificial sequence
<220> FEATURE:
<223> OTHER INFORMATION: Synthetic Peptide

<400> SEQUENCE: 55

```
Phe Val Gln Asp His Phe Asp His Asn Ile Ser Pro Thr Ile Gly
1               5                   10                  15
```

<210> SEQ ID NO 56
<211> LENGTH: 48
<212> TYPE: RNA
<213> ORGANISM: Artificial sequence
<220> FEATURE:

```
<223> OTHER INFORMATION: Synthetic Polynucleotide

<400> SEQUENCE: 56
ggagacaugu uccacaggca ucgaaaugcc uguggaacau gucuccuu          48
```